(12) United States Patent
Liu et al.

(10) Patent No.: US 11,298,330 B2
(45) Date of Patent: Apr. 12, 2022

(54) MAGNESIUM COMPOSITIONS AND METHODS OF USE

(71) Applicant: Neurocentria, Inc., Walnut Creek, CA (US)

(72) Inventors: Guosong Liu, Oakland, CA (US); Fei Mao, Fremont, CA (US); Jason Weinger, Concord, CA (US)

(73) Assignee: Neurocentria, Inc., Fremont, CA (US)

(*) Notice: Subject to any disclaimer, the term of this patent is extended or adjusted under 35 U.S.C. 154(b) by 201 days.

(21) Appl. No.: 16/663,993

(22) Filed: Oct. 25, 2019

(65) Prior Publication Data

US 2020/0121624 A1 Apr. 23, 2020

Related U.S. Application Data

(63) Continuation of application No. PCT/US2018/029664, filed on Apr. 26, 2018.

(60) Provisional application No. 62/490,569, filed on Apr. 26, 2017.

(51) Int. Cl.
| | | |
|---|---|---|
| *A61K 31/191* | (2006.01) | |
| *A61K 9/20* | (2006.01) | |
| *A61P 25/28* | (2006.01) | |

(52) U.S. Cl.
CPC ............. *A61K 31/191* (2013.01); *A61K 9/20* (2013.01); *A61P 25/28* (2018.01)

(58) Field of Classification Search
CPC .......... A61K 31/191; A61K 9/20; A61P 25/28
USPC ........................................................ 514/557
See application file for complete search history.

(56) References Cited

U.S. PATENT DOCUMENTS

| | | |
|---|---|---|
| 3,992,518 A | 11/1976 | Chien et al. |
| 4,284,444 A | 8/1981 | Bernstein et al. |
| 4,327,725 A | 5/1982 | Cortese et al. |
| 4,606,909 A | 8/1986 | Bechgaard et al. |
| 4,769,027 A | 9/1988 | Baker et al. |
| 4,861,800 A | 8/1989 | Buyske |
| 4,897,268 A | 1/1990 | Tice et al. |
| 4,985,256 A | 1/1991 | Glick |
| 5,186,938 A | 2/1993 | Sablotsky et al. |
| 5,395,626 A | 3/1995 | Kotwal et al. |
| 5,422,120 A | 6/1995 | Kim |
| 5,422,123 A | 6/1995 | Conte et al. |
| 5,601,845 A | 2/1997 | Buxton et al. |
| 5,660,848 A | 8/1997 | Moo-Young |
| 5,756,115 A | 5/1998 | Moo-Young et al. |
| 5,912,013 A | 6/1999 | Rudnic et al. |
| 6,183,770 B1 | 2/2001 | Muchin et al. |
| 6,194,000 B1 | 2/2001 | Smith et al. |
| 6,635,268 B2 | 10/2003 | Peery et al. |
| 6,715,485 B1 | 4/2004 | Djupesland |
| 6,743,211 B1 | 6/2004 | Prausnitz et al. |
| 6,764,697 B1 | 7/2004 | Jao et al. |
| 6,797,283 B1 | 9/2004 | Edgren et al. |
| 6,919,373 B1 | 7/2005 | Lam et al. |
| 6,923,800 B2 | 8/2005 | Chen et al. |
| 6,929,803 B2 | 8/2005 | Wong et al. |
| 6,939,556 B2 | 9/2005 | Lautenbach |
| 6,945,952 B2 | 9/2005 | Kwon |
| 2005/0129762 A1 | 6/2005 | Heaton et al. |
| 2006/0051416 A1 | 3/2006 | Rastogi et al. |
| 2006/0292221 A1 | 12/2006 | Sawada et al. |
| 2007/0065512 A1 | 3/2007 | Dedhiya et al. |
| 2007/0128279 A1 | 6/2007 | Edgren et al. |
| 2011/0020443 A1 | 1/2011 | Liu et al. |
| 2014/0200176 A1 | 7/2014 | Berg |
| 2014/0342021 A1 | 11/2014 | Liu et al. |
| 2016/0250169 A1 | 9/2016 | Perez et al. |
| 2017/0106016 A1 | 4/2017 | Liu et al. |

FOREIGN PATENT DOCUMENTS

| | | |
|---|---|---|
| EP | 0524968 B1 | 6/1995 |
| WO | WO-8909051 A1 | 10/1989 |
| WO | WO-9114445 A1 | 10/1991 |
| WO | WO-9513796 A1 | 5/1995 |
| WO | WO-2017044486 A1 | 3/2017 |
| WO | WO-2018200885 A1 | 11/2018 |

OTHER PUBLICATIONS

Andrasi, et al. Brain aluminum, magnesium and phosphorus contents of control and Alzheimer-diseased patients. J Alzheimers Dis. Aug. 2005. 7(4):273-84.

Badawy, et al. Cortical excitability and neurology: insights into the pathophysiology. Funct Neurol. Jul.-Sep. 2012. 27(3):131-145.

Bateman, et al. Human amyloid-beta synthesis and clearance rates as measured in cerebrospinal fluid in vivo. Nat Med. Jul. 2006. 12(7):856-61. Epub Jun. 25, 2006. DOI: 10.1038/nm1438.

Chen, et al. Ultrasensitive fluorescent proteins for imaging neuronal activity. Nature. vol. 499. pp. 295-300. Jul. 2013. DOI: 10.1038/nature12354.

Cilliler, et al. Serum Magnesium Level and Clinical Deterioration in Alzheimer's Disease. Gerontology. Nov. 8, 2007;53(6):419-422.

(Continued)

*Primary Examiner* — Kristin A Vajda
(74) *Attorney, Agent, or Firm* — Wilson, Sonsini, Goodrich and Rosati

(57) ABSTRACT

The present invention provides a method of administering magnesium threonate to a subject in need of supplementing magnesium. At least a portion of magnesium (Mg) and threonate (T) is present in a salt form of $MgT_2$. The method may comprise administration of magnesium threonate at two different time points per day. The method may comprise administering, at a first time point, a first oral dosage form comprising magnesium threonate. The method may comprise administering, at a second time point, a combination of the first oral dosage form and a second oral dosage form comprising magnesium threonate. The first and second oral dosage forms may exhibit different dissolution profiles in a dissolution medium.

19 Claims, 5 Drawing Sheets

(56) References Cited

OTHER PUBLICATIONS

Cirrito, et al. Endocytosis is required for synaptic activity-dependent release of amyloid-beta in vivo. Neuron. Apr. 10, 2008. 58(1):42-51. doi: 10.1016/j.neuron.2008.02.003.

Cirrito, et al. Synaptic activity regulates interstitial fluid amyloid-beta levels in vivo. Neuron. Dec. 22, 2005. 48(6):913-22. DOI 10.1016/j.neuron.2005.10.028.

De Lourdes Lima, et al. The effect of magnesium supplementation in increasing doses on the control of type 2 diabetes. Diabetes Care. May 1998;21(5):682-686. DOI: 10.2337/diacare.21.5.682.

Di Lazzaro, et al. Motor cortex hyperexcitability to transcranial magnetic stimulation in Alzheimer's disease. J Neurol Neurosurg Psychiatry. Apr. 2004. 75(4):555-559. doi: 10.1136/jnnp.2003. 018127.

Eibl, et al. Magnesium supplementation in type 2 diabetes. Diabetes Care. Nov. 1998. 21(11):2031-2032. https://doi.org/10.2337/diacare.21.11.2031.

Facchinetti, et al. Magnesium prophylaxis of menstrual migraine: effects on intracellular magnesium. Headache. May 1991. 31(5):298-301. DOI: 10.1111/j.1526-4610.1991.hed3105298.x.

Folstein, et al. "Mini-mental state". A practical method for grading the cognitive state of patients for the clinician. J Psychiatr Res. Nov. 1975. 12(3):189-98. DOI: 10.1016/0022-3956(75)90026-6.

Gorgoni, et al. Sleep deprivation affects somatosensory cortex excitability as tested through median nerve stimulation. Brain Stimul. Sep.-Oct. 2014. 7(5):732-9. doi: 10.1016/j.brs.2014.04.006. Epub May 23, 2014.

Haimov, et al. Sleep disorders and melatonin rhythms in elderly people. BMJ. Jul. 16, 1994. 309(6948):167. DOI: 10.1136/bmj.309. 6948.167.

Hartmann, et al. Twenty-four hour cortisol release profiles in patients with Alzheimer's and Parkinson's disease compared to normal controls: ultradian secretory pulsatility and diurnal variation. Neurobiol Aging. May-Jun. 1997. 18(3):285-289. DOI: 10.1016/s0197-4580(97)80309-0.

Houx, et al. Testing cognitive function in elderly populations: the PROSPER study. J Neurol Neurosurg Psychiatry. Oct. 2002. 73(4):385-389. DOI: 10.1136/jnnp.73.4.385.

Huber, et al. Human cortical excitability increases with time awake. Cereb Cortex. Feb. 2013. 23(2):332-338. doi: 10.1093/cercor/bhs014. Epub Feb. 7, 2012.

International search report with written opinion dated Jul. 31, 2018 for PCT/US18/29664.

Kang, et al. Amyloid-beta dynamics are regulated by orexin and the sleep-wake cycle. Science. Nov. 13, 2009. 326(5955):1005-1007. doi: 10.1126/science. 1180962. Epub Sep. 24, 2009.

Khedr, et al. The relationship between motor cortex excitability and severity of Alzheimer's disease: a transcranial magnetic stimulation study. Neurophysiol Clin. Jul. 2011;41(3):107-13. doi: 10.1016/j.neucli.2011.03.002. Epub Apr. 19, 2011.

Kim, et al. Growth hormone rescues hippocampal synaptic function after sleep deprivation. Am J Physiol Regul Integr Comp Physiol. Jun. 2010;298(6):R1588-96. doi: 10.1152/ajpregu.00580.2009. Epub Mar. 17, 2010.

Kozielec, et al., Assessment of magnesium levels in children with attention deficit hyperactivity disorder (ADHD). Magnes Res. Jun. 1997;10(2):143-8. Abstract Only.

Landfield, et al. Chronically elevating plasma Mg2+ improves hippocampal frequency potentiation and reversal learning in aged and young rats. Brain Res. Nov. 19, 1984. 322(1):167-171.

Lee, et al. Memory of sequential experience in the hippocampus during slow wave sleep. Neuron. Dec. 19, 2002. 36(6):1183-1194. DOI: 10.1016/s0896-6273(02)01096-6.

Lemke, M.R. Plasma magnesium decrease and altered calcium/magnesium ratio in severe dementia of the Alzheimer type. Biol Psychiatry. Mar. 1, 1995. 37(5):341-343. DOI: 10.1016/0006-3223(94)00241-T.

Lim, et al. Sleep is related to neuron numbers in the ventrolateral preoptic/intermediate nucleus in older adults with and without Alzheimer's disease. Brain. Oct. 2014. 137(Pt 10):2847-2861. doi: 10.1093/brain/awu222. Epub Aug. 20, 2014.

List, et al. Relationship between excitability, plasticity and thickness of the motor cortex in older adults. Neuroimage. Dec. 2013. 83:809-816. doi: 10.1016/j.neuroimage.2013.07.033. Epub Jul. 19, 2013.

Ly, et al. Circadian regulation of human cortical excitability. Nat Commun. Jun. 24, 2016. 7:11828. doi:10.1038/ncomms11828.

Malhotra, et al. The therapeutic potential of melatonin: a review of the science. MedGenMed. Apr. 13, 2004. 6(2):46.

Mander, et al. Sleep and Human Aging. Neuron. Apr. 5, 2017. 94(1):19-36. doi: 10.1016/j.neuron.2017.02.004.

Martineau, et al. Vitamin B6, magnesium, and combined B6-Mg: Therapeutic effects in childhood autism. Biological Psychiatry. May 1985. vol. 20. Issue 5. pp. 467-478. DOI: https://doi.org/10.1016/0006-3223(85)90019-8.

Mawuenyega, et al. Decreased clearance of CNS beta-amyloid in Alzheimer's disease. Science. Dec. 24, 2010. 330(6012):1774. doi: 10.1126/science.1197623. Epub Dec. 9, 2010.

Mizuno, et al. Acetylcholine release in the rat hippocampus as measured by the microdialysis method correlates with motor activity and exhibits a diurnal variation. Neuroscience. 1991. 44(3):607-12. DOI: 10.1016/0306-4522(91)90081-x.

Mousain-Bosc, et al. Improvement of neurobehavioral disorders in children supplemented with magnesium-vitamin B6. I. Attention deficit hyperactivity disorders. Magnes Res. Mar. 2006. 19(1):46-52.

Murck, H. Magnesium and affective disorders. Nutr Neurosci. Dec. 2002. 5(6):375-389. doi: 10.1080/1028415021000039194.

Olazaran, et al. Cortical excitability in very mild Alzheimer's disease: a long-term follow-up study. J Neurol. Dec. 2010. 257(12):2078-2085. doi: 10.1007/s00415-010-5663-8. Epub Jul. 31, 2010.

Oliviero, et al. Effects of aging on motor cortex excitability. Neurosci Res. May 2006. 55(1):74-7. Epub Apr. 3, 2006. DOI: 10.1016/j.neures.2006.02.002.

Ooms, et al. Effect of 1 night of total sleep deprivation on cerebrospinal fluid β-amyloid 42 in healthy middle-aged men: a randomized clinical trial. JAMA Neurol. Aug. 2014;71(8):971-7. doi: 10.1001/jamaneurol.2014.1173.

Pandi-Perumal, et al. Physiological effects of melatonin: role of melatonin receptors and signal transduction pathways. Prog Neurobiol. Jul. 2008. 85(3):335-353. doi: 10.1016/j.pneurobio.2008.04.001. Epub Apr. 16, 2008.

Peigneux, et al. Are spatial memories strengthened in the human hippocampus during slow wave sleep? Neuron. Oct. 28, 2004. 44(3):535-45. DOI: 10.1016/j.neuron.2004.10.007.

Pennisi, et al. Transcranial magnetic stimulation in Alzheimer's disease: a neurophysiological marker of cortical hyperexcitability. J Neural Transm (Vienna). Apr. 2011. 118(4):587-598. doi: 10.1007/S00702-010-0554-9. Epub Jan. 5, 2011.

Peuhkuri, et al. Dietary factors and fluctuating levels of melatonin. Food Nutr Res. Jul. 20, 2012. 56. doi: 10.3402/fnr.v56i0.17252. Epub Jul. 20, 2012.

Pfeiffer, et al. Efficacy of vitamin B6 and magnesium in the treatment of autism: a methodology review and summary of outcomes. J Autism Dev Disord. Oct. 1995. 25(5):481-93. DOI: 10.1007/bf02178295.

Ramadan, et al. Low brain magnesium in migraine. Headache. Oct. 1989. 29(9):590-593. DOI: 10.1111/j.1526-4610.1989.hed2909590.x.

Robinson, D. Implications of neural networks for how we think about brain function. Behavioral and Brain Sciences. Dec. 1992. 15(4). pp. 644-655. DOI: 10.1017/S0140525X00072563.

Roh, et al. Disruption of the sleep-wake cycle and diurnal fluctuation of β-amyloid in mice with Alzheimer's disease pathology. Sci Transl Med. Sep. 5, 2012. 4(150):150ra122. doi: 10.1126/scitranslmed. 3004291.

Schmid, H.A. Decreased melatonin biosynthesis, calcium flux, pineal gland calcification and aging: a hypothetical framework. Gerontology. 1993. 39(4):189-99. DOI: 10.1159/000213533.

Skene, et al. Melatonin rhythmicity: effect of age and Alzheimer's disease. Exp Gerontol. Jan.-Feb. 2003. 38(1-2):199-206. DOI: 10.1016/s0531-5565(02)00198-5.

(56) References Cited

OTHER PUBLICATIONS

Slutsky, et al. Enhancement of synaptic plasticity through chronically reduced Ca2+ flux during uncorrelated activity. Neuron. Dec. 2, 2004. 44(5):835-49. DOI: 10.1016/j.neuron.2004.11.013.
Strambi, et al. Magnesium profile in autism. Biol Trace Elem Res. Feb. 2006. 109(2):97-104. DOI: 10.1385/BTER:109:2:097.
Takaya, et al. Effects of insulin and insulin-like growth factor-1 on intracellular magnesium of platelets. Exp Mol Pathol. Oct. 1998. 65(2):104-9. DOI: 10.1006/exmp.1998.2232.
Thomas, et al. Evaluation of threonic acid toxicity in small animals. Food Chemistry. 1985. 17(2):79-83 DOI: 10.1016/0308-8146(85)90076-7.
Torres, et al. Involvement of ERK1/2 and p38 in Mg2+ accumulation in liver cells. Mol Cell Biochem. Aug. 2006. 288(1-2):191-9. Epub May 2, 2006. DOI: 10.1007/s11010-006-9139-1.
U.S. Department of Health and Human Services Food and Drug Administration. Dissolution Testing of Immediate Release Solid Oral Dosage Forms. Guidance for Industry. Center for Drug Evaluation and Research (CDER). Aug. 1997. Section IV-A.
U.S. Department of Health and Human Services Food and Drug Administration. Extended Release Oral Dosage Forms: Development, Evaluation, and Application of In Vitro/In Vivo Correlations. Guidance for Industry. Center for Drug Evaluation and Research (CDER). Sep. 1997. pp. 4, 17.
U.S. Department of Health and Human Services Food and Drug Administration. SUPAC-MR: Modified Release Solid Oral Dosage Forms. Guidance for Industry. Center for Drug Evaluation and Research (CDER). Sep. 1997. p. 6.
Van Cauter, et al. Age-Related Changes in Slow Wave Sleep and REM Sleep and Relationship With Growth Hormone and Cortisol Levels in Healthy Men. JAMA. Aug. 16, 2000. 284(7):861-868. doi:10.1001/jama.284.7.861.
Van Cauter, et al. Effects of gender and age on the levels and circadian rhythmicity of plasma cortisol. J Clin Endocrinol Metab. Jul. 1996. 81(7):2468-2473. DOI: 10.1210/jcem.81.7.8675562.
Verlangieri, et al. Comparison of the anti-scorbutic activity of L-ascorbic acid and Ester C in the non-ascorbate synthesizing Osteogenic Disorder Shionogi (ODS) rat. Life Sci. 1991. 48(23):2275-2281. DOI: 10.1016/0024-3205(91)90343-a.
Wang, et al. Pharmacokinetics and safety of calcium L-threonate in healthy volunteers after single and multiple oral administrations. Acta Pharmacol Sin. Dec. 2011. 32(12):1555-1560. doi: 10.1038/aps.2011.138. Epub Oct. 10, 2011.
Wei, et al. Synaptic Mechanisms of Memory Consolidation during Sleep Slow Oscillations. J Neurosci. Apr. 13, 2016. 36(15): 4231-4247. doi: 10.1523/JNEUROSCI.3648-15.2016.
Wood, et al. Reorganization of verbal memory and language: a case of dissociation. J Int Neuropsychol Soc. Jan. 1999. 5(1):69-74. DOI: 10.1017/s1355617799511090.
Wroolie, et al. An 8-week open label trial of l-Threonic Acid Magnesium Salt in patients with mild to moderate dementia. Personalized Medicine in Psychiatry. vols. 4-6. Dec. 2017. pp. 7-12. https://doi.org/10.1016/j.pmip.2017.07.001.
Wu, et al. Pineal clock gene oscillation is disturbed in Alzheimer's disease, due to functional disconnection from the "master clock". FASEB J. Sep. 2006. 20(11):Full text E1171-E1180. Summary 1874-1876. Epub Jul. 3, 2006. doi: 10.1096/fj.05-4446fje.
Xie et al. Sleep drives metabolite clearance from the adult brain. Science 342(6156):373-377 (2013).
Zhou, et al. Regulation of density of functional presynaptic terminals by local energy supply. Mol Brain. Jul. 17, 2015. 8:42. doi: 10.1186/s13041-015-0132-z.

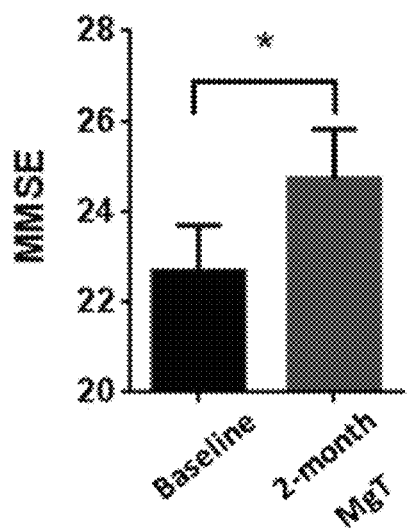
FIG. 5A
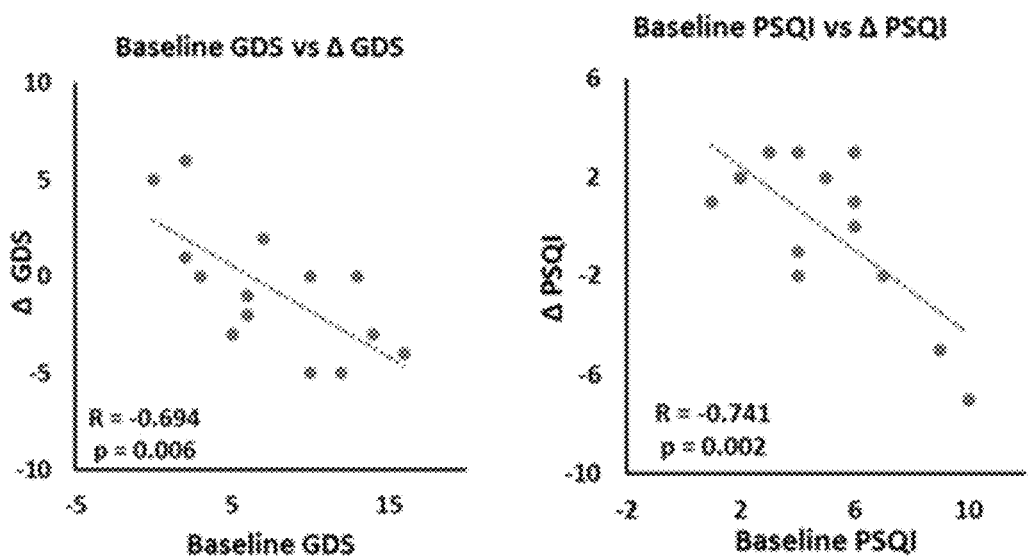
FIG. 5B
FIG. 5C

MAGNESIUM COMPOSITIONS AND METHODS OF USE

CROSS-REFERENCE

This application is a continuation of International Patent Application No. PCT/US2018/029664, filed Apr. 26, 2018, which claims the benefit of U.S. Patent Application No. 62/490,569, filed Apr. 26, 2017, each of which is entirely incorporated herein by reference.

BACKGROUND

Magnesium is the one of the most abundant mineral in the human body and plays multiple roles in maintaining good health. Examples of the roles of magnesium in living cells include homeostasis of other minerals, such as sodium, potassium and calcium, as well as the formation, transfer, storage and utilization of adenosine triphosphate (ATP), a principal source of energy in living cells. Other functions of magnesium in the human body include the maintenance of normal muscle and nerve activity, heart rhythm, bone strength, and immune system health.

It has been estimated that a majority of the people in the U.S. may not be taking sufficient magnesium and hence may be magnesium deficient. Magnesium deficiency including hypomagnesia refers to inadequate intake of dietary magnesium or impaired absorption of magnesium. Magnesium deficiency is also associated with numerous symptoms and diseases, including hypertension, atherosclerosis, arrhythmia, diabetes, and metabolic syndromes. Magnesium deficiency may also be correlated with neurological disorders, including dementia, Alzheimer's disease, and depression.

Magnesium deficiency may be ameliorated by oral supplements. Examples of conventional magnesium supplements include magnesium oxide tablets or capsules, and various inorganic magnesium compounds, such as magnesium hydroxide and magnesium sulfate. To supply the population with sufficient magnesium, a very high dose of magnesium supplement may typically be required to reach the recommended daily allowance (RDA). For example, 4 grams of magnesium oxide may be required as an oral supplement. Use of this and other conventional magnesium supplements to reach the RDA may suffer from a number of drawbacks, including a poor absorption rate in the human body (i.e., bioavailability) and diarrhea, thereby rending them not feasible for chronic use. Alternative magnesium supplements, including magnesium-counter ion compounds (e.g., magnesium lactate and magnesium threonate) have been reported. Amongst the various magnesium compounds, magnesium threoate has the highest bioavailability, making it useful for treating magnesium deficiency including the associated disease conditions.

SUMMARY

There still exists a considerable need for alternative dosage forms of magnesium supplements and methods of delivery to provide desired physiological benefits. For treating neurological disorder or improving overall brain function in non-diseased people, immediate release capsule formulation of magnesium threonate may not be adequate for achieving the desired high efficacy/safety ratio. In one aspect, a desired formulation for treating neurological disorder or improving overall brain health is one that can generate controlled treatment effects over a 24 hr time period, which effects an immediate release magnesium threonate is unable to achieve. The present invention provides a unique combination of two formulations with different release profiles of magnesium threonate that generates a unique release profile of magnesium threonate.

According to an aspect of the invention, a method of administering magnesium threonate to a subject in need of supplementing magnesium is provided. In some embodiments, at least a portion of magnesium (Mg) and threonate (T) of the magnesium threonate may be present in a salt form of $MgT_2$. In some embodiments, the method may comprise administering, at two different time points per day, (a) a first oral dosage form comprising magnesium threonate, and (b) a combination of (i) the first oral dosage form and (ii) a second oral dosage form comprising magnesium threonate, which first and second oral dosage forms exhibit different in vitro dissolution profiles in a dissolution medium. In some embodiments, the magnesium threonate may be present in an amount between about 200 mg to 2000 mg in each of the first and second oral dosage forms.

In some embodiments, a first in vitro dissolution profile of the first oral dosage form in the dissolution medium may be slower than a second in vitro dissolution profile of the second oral dosage form in the dissolution medium, as measured using a USP type II (paddle) dissolution system at 75 rpm, at a temperature of about 37° C.

In some embodiments, the first in vitro dissolution profile may range about 10% to 35% in about 1 hour. In some embodiments, the first in vitro dissolution profile may range about 20% to 50% in about 2 hours. In some embodiments, the first in vitro dissolution profile may be greater than about 80% in about 4 hours. In some embodiments, the first in vitro dissolution profile may be greater than about 90% in about 6 hours. In some embodiments, the first in vitro dissolution profile may be greater or equal to about 95% in about 8 hours. In some embodiments, the first in vitro dissolution profile may range between (i) about 10 to 35% in about 1 hour, (ii) about 20% to 50% in about 2 hours, (iii) greater than about 80% in about 4 hours, (iv) greater than about 90% in about 6 hours, and (v) greater or equal to about 95% in about 8 hours.

In some embodiments, the second in vitro dissolution profile may be greater than or equal to about 50% in about 0.5 hour. In some embodiments, the second in vitro dissolution profile may be greater or equal to about 80% in about 1 hour. In some embodiments, the second in vitro dissolution profile may range between (i) greater than or equal to about 50% in about 0.5 hour and (ii) greater or equal to about 80% in about 1 hour.

In some embodiments, the combination of the first and second oral dosage form may exhibit a third in vitro dissolution profile ranging about 50% to 75% in about 1 hour. In some embodiments, the combination of the first and second oral dosage form may exhibit a third in vitro dissolution profile greater than about 60% in about 2 hours. In some embodiments, the combination of the first and second oral dosage form may exhibit a third in vitro dissolution profile greater than about 80% in about 4 hours. In some embodiments, the combination of the first and second oral dosage form may exhibit a third in vitro dissolution profile ranging between (i) about 50% to 75% in about 1 hour, (ii) greater than about 60% in about 2 hours, and (iii) greater than about 80% in about 4 hours.

In some embodiments, a first in vitro dissolution profile of the first oral dosage form in the dissolution medium may be faster than a second in vitro dissolution profile of the second oral dosage form in the dissolution medium, as measured using a USP type II (paddle) dissolution system at 75 rpm, at a temperature of about 37° C.

In some embodiments, the first in vitro dissolution profile may be greater than or equal to about 50% in about 0.5 hour. In some embodiments, the first in vitro dissolution profile may be greater or equal to about 80% in about 1 hour. In some embodiments, the first in vitro dissolution profile may range between (i) greater than or equal to about 50% in about 0.5 hour and (ii) greater or equal to about 80% in about 1 hour.

In some embodiments, the second in vitro dissolution profile may be about 10% to 35% in about 1 hour. In some embodiments, the second in vitro dissolution profile may be about 20 to 50% in about 2 hours. In some embodiments, the second in vitro dissolution profile may be greater than about 80% in about 4 hours. In some embodiments, the second in vitro dissolution profile may be greater than about 90% in about 6 hours. In some embodiments, the second in vitro dissolution profile may be greater or equal to about 95% in about 8 hours. In some embodiments, the second in vitro dissolution profile may range between (i) about 10% to 35% in about 1 hour, (ii) about 20% to 50% in about 2 hours, (iii) greater than about 80% in about 4 hours, (iv) greater than about 90% in about 6 hours, and (v) greater or equal to about 95% in about 8 hours.

In some embodiments, the combination of the first and second oral dosage form may exhibit a third in vitro dissolution profile ranging about 50% to 75% in about 1 hour. In some embodiments, the combination of the first and second oral dosage form may exhibit a third in vitro dissolution profile greater than about 60% in about 2 hours. In some embodiments, the combination of the first and second oral dosage form may exhibit a third in vitro dissolution profile greater than about 80% in about 4 hours. In some embodiments, the combination of the first and second oral dosage form may exhibit a third in vitro dissolution profile ranging between (i) about 50% to 75% in about 1 hour, (ii) greater than about 60% in about 2 hours, and (iii) greater than about 80% in about 4 hours.

In some embodiments, the magnesium threonate may be present in at least an amount to improve a Mini-Mental State Examination (MMSE) score of the subject. In some embodiments, the method may further comprise determining the MMSE score of the subject prior to starting a regimen of the first and second oral dosage forms. In some embodiments, the method may further comprise determining the MMSE score of the subject subsequent to starting the regimen of the first and second oral dosage forms.

In some embodiments, the first and second oral dosage forms may have substantially the same amount of magnesium threonate.

In some embodiments, each of the first and second oral dosage forms may be liquid, semi-liquid, semi-solid, or solid. In some embodiments, each of the first and second oral dosage forms may be a gel, pill, tablet, capsule, bead, emulsion, granule, paste, prill, powder, syrup, suspension, slurry, or aerosol.

In some embodiments, each of the first and second oral dosage forms may further comprise an additional agent. In some embodiments, the additional agent may be a pharmaceutically acceptable carrier. In some embodiments, the pharmaceutically acceptable carrier may be selected from the group consisting of micelles, liposomes, microspheres, nanofibers, and any combination thereof. In some embodiments, the additional agent may be a pharmaceutically acceptable excipient. In some embodiments, the pharmaceutically acceptable excipient may be selected from the group consisting of a binder, filler, lubricant, dissolution aid, and any combination thereof. In some embodiments, the pharmaceutically acceptable excipient may be selected from the group consisting of lactose, microcrystalline cellulose, silicon dioxide, titanium dioxide, stearic acid, starch, sodium starch glycolate, povidone, pregelatinized starch, croscarmellose, ethylcellulose, calcium phosphate, talc, sucrose, calcium stearate, magnesium stearate, hydroxypropyl methylcellulose, shellac, hydrogenated vegetable oil, carnauba wax, beeswax, and any combination thereof. In some embodiments, the additional agent may be a nutritionally active agent. In some embodiments, the nutritionally active agent may be selected from the group consisting of a calcium-containing material, an herbal, a spice, vitamin A, vitamin B, vitamin C, vitamin D, vitamin E, vitamin K, niacin, folic acid, biotin, a mineral, and any combination thereof.

In some embodiments, the method of administering magnesium threonate to the subject in need of supplementing magnesium may comprise (a) administering a first oral dosage form comprising magnesium threonate and (b) administering a combination of (i) the first oral dosage form and (ii) a second oral dosage form comprising magnesium threonate. In some embodiments, the method may further comprise (c) repeating (a) and (b) for at least about 15 days. In some embodiments, the method may further comprise (c) repeating (a) and (b) for at least about 1 month. In some embodiments, the method may further comprise (c) repeating (a) and (b) for a period of greater than 3 months.

In some embodiments, the first and second oral dosage forms may be administered as dietary supplements.

In some embodiments, the subject to be administered with the subject dosage forms may be an adult. In some embodiments, the subject may suffer from magnesium deficiency, mild cognitive impairment, short-term memory loss, long-term memory loss, Alzheimer's disease, Parkinson's disease, Huntington's disease, autism, schizophrenia, cognitive decline, depression, dementia, attention deficit hyperactivity disorder (ADHD), amyotrophic lateral sclerosis (ALS), diabetes, cardiovascular disease, hypertension, migraine, glaucoma, mood disorder, stress, anxiety, depression, sleep disorder, metabolic disorder, fatigue, cancer, HIV, hepatitis, spinal cord injury, post-surgery recovery, post-traumatic stress disorder, arthritis, neuropathic pain, inflammation, and/or tremor.

According to another aspect of the invention, a kit for administering magnesium threonate to a subject in need of supplementing magnesium is provided. In some embodiments, at least a portion of magnesium (Mg) and threonate (T) of the magnesium threonate may be present in a salt form of $MgT_2$. In some embodiments, the kit may comprise (a) two of a first oral dosage form comprising magnesium threonate, (b) one of a second oral dosage form comprising magnesium threonate, which first and second oral dosage forms exhibit different in vitro dissolution profiles in a dissolution medium, and (c) a set of instructions for instructing the subject on (i) consuming the first oral dosage form in daytime, and (ii) consuming a combination of the first and second oral dosage forms at once in nighttime. In some embodiments, the first and second oral dosage forms may have the magnesium threonate in an amount between about 200 mg to 2000 mg.

In some embodiments, the kit may be formulated such that the kit provides an amount of the first and second oral dosage forms to be utilized by the subject for at least one month.

In some embodiments, a first in vitro dissolution profile of the first oral dosage form in the dissolution medium may be slower than a second in vitro dissolution profile of the second oral dosage form in the dissolution medium, as measured using a USP type II (paddle) dissolution system at 75 rpm, at a temperature of about 37° C.

In some embodiments, the first in vitro dissolution profile may range about 10% to 35% in about 1 hour. In some embodiments, the first in vitro dissolution profile may range about 20% to 50% in about 2 hours. In some embodiments, the first in vitro dissolution profile may be greater than about 80% in about 4 hours. In some embodiments, the first in vitro dissolution profile may be greater than about 90% in about 6 hours. In some embodiments, the first in vitro dissolution profile may be greater or equal to about 95% in about 8 hours. In some embodiments, the first in vitro dissolution profile may range between (i) about 10% to 35% in about 1 hour, (ii) about 20% to 50% in about 2 hours, (iii) greater than about 80% in about 4 hours, (iv) greater than about 90% in about 6 hours, and (v) greater or equal to about 95% in about 8 hours.

In some embodiments, the second in vitro dissolution profile may be greater than or equal to about 50% in about 0.5 hour. In some embodiments, the second in vitro dissolution profile may be greater or equal to about 80% in about 1 hour. In some embodiments, the second in vitro dissolution profile may range between (i) greater than or equal to about 50% in about 0.5 hour and (ii) greater or equal to about 80% in about 1 hour.

In some embodiments, the combination of the first and second oral dosage form may exhibit a third in vitro dissolution profile ranging about 50% to 75% in about 1 hour. In some embodiments, the combination of the first and second oral dosage form may exhibit a third in vitro dissolution profile greater than about 60% in about 2 hours. In some embodiments, the combination of the first and second oral dosage form may exhibit a third in vitro dissolution profile greater than about 80% in about 4 hours. In some embodiments, the combination of the first and second oral dosage form may exhibit a third in vitro dissolution profile ranging between (i) about 50% to 75% in about 1 hour, (ii) greater than about 60% in about 2 hours, and (iii) greater than about 80% in about 4 hours.

In some embodiments, a first in vitro dissolution profile of the first oral dosage form in the dissolution medium may be faster than a second in vitro dissolution profile of the second oral dosage form in the dissolution medium, as measured using a USP type II (paddle) dissolution system at 75 rpm, at a temperature of about 37° C.

In some embodiments, the first in vitro dissolution profile may be greater than or equal to about 50% in about 0.5 hour. In some embodiments, the first in vitro dissolution profile may be greater or equal to about 80% in about 1 hour. In some embodiments, the first in vitro dissolution profile may range between (i) greater than or equal to about 50% in about 0.5 hour and (ii) greater or equal to about 80% in about 1 hour.

In some embodiments, the second in vitro dissolution profile may be about 10% to 35% in about 1 hour. In some embodiments, the second in vitro dissolution profile may be about 20% to 50% in about 2 hours. In some embodiments, the second in vitro dissolution profile may be greater than about 80% in about 4 hours. In some embodiments, the second in vitro dissolution profile may be greater than about 90% in about 6 hours. In some embodiments, the second in vitro dissolution profile may be greater or equal to about 95% in about 8 hours. In some embodiments, the second in vitro dissolution profile may range between (i) about 10% to 35% in about 1 hour, (ii) about 20% to 50% in about 2 hours, (iii) greater than about 80% in about 4 hours, (iv) greater than about 90% in about 6 hours, and (v) greater or equal to about 95% in about 8 hours.

In some embodiments, the combination of the first and second oral dosage form may exhibit a third in vitro dissolution profile ranging about 50% to 75% in about 1 hour. In some embodiments, the combination of the first and second oral dosage form may exhibit a third in vitro dissolution profile greater than about 60% in about 2 hours. In some embodiments, the combination of the first and second oral dosage form may exhibit a third in vitro dissolution profile greater than about 80% in about 4 hours. In some embodiments, the combination of the first and second oral dosage form may exhibit a third in vitro dissolution profile ranging between (i) about 50% to 75% in about 1 hour, (ii) greater than about 60% in about 2 hours, and (iii) greater than about 80% in about 4 hours.

In some embodiments, the magnesium threonate in the kit may be present in at least an amount to improve a Mini-Mental State Examination (MMSE) score of the subject. In some embodiments, the method may further comprise determining the MMSE score of the subject prior to starting a regimen of the first and second oral dosage forms. In some embodiments, the method may further comprise determining the MMSE score of the subject subsequent to starting the regimen of the first and second oral dosage forms.

In some embodiments, the kit may further comprise an additional set of instructions for evaluating the MMSE score. In some embodiments, the kit may further comprise an additional set of instructions for determining the MMSE score of the subject prior to starting a regimen of the first and second oral dosage forms. In some embodiments, the kit may further comprise an additional set of instructions for determining the MMSE score of the subject subsequent to starting the regimen of the first and second oral dosage forms.

In some embodiments, the first and second oral dosage forms may have substantially the same amount of magnesium threonate.

In some embodiments, each of the first and second oral dosage forms may be liquid, semi-liquid, semi-solid, or solid. In some embodiments, each of the first and second oral dosage forms may be a gel, pill, tablet, capsule, bead, emulsion, granule, paste, prill, powder, syrup, suspension, slurry, or aerosol.

In some embodiments, each of the first and second oral dosage forms may further comprise an additional agent. In some embodiments, the additional agent may be a pharmaceutically acceptable carrier. In some embodiments, the pharmaceutically acceptable carrier may be selected from the group consisting of micelles, liposomes, microspheres, nanofibers, and any combination thereof. In some embodiments, the additional agent may be a pharmaceutically acceptable excipient. In some embodiments, the pharmaceutically acceptable excipient may be selected from the group consisting of a binder, filler, lubricant, dissolution aid, and any combination thereof. In some embodiments, the pharmaceutically acceptable excipient may be selected from the group consisting of lactose, microcrystalline cellulose, silicon dioxide, titanium dioxide, stearic acid, starch, sodium starch glycolate, povidone, pregelatinized starch, croscarmellose, ethylcellulose, calcium phosphate, talc, sucrose, calcium stearate, magnesium stearate, hydroxypropyl methylcellulose, shellac, hydrogenated vegetable oil, carnauba wax, beeswax, and any combination thereof. In some embodiments, the additional agent may be a nutritionally active agent. In some embodiments, the nutritionally active agent may be selected from the group consisting of a calcium-containing material, an herbal, a spice, vitamin A, vitamin B, vitamin C, vitamin D, vitamin E, vitamin K, niacin, folic acid, biotin, a mineral, and any combination thereof.

In some embodiments, the kit may comprise a set of instructions for instructing the subject on (i) consuming the first oral dosage form in daytime, (ii) consuming a combination of the first and second oral dosage forms at once in nighttime, and (c) repeating (i) and (ii) for at least about 15 days. In some embodiments, the kit may comprise a set of instructions for instructing the subject on (i) consuming the first oral dosage form in daytime, (ii) consuming a combination of the first and second oral dosage forms at once in nighttime, and (c) repeating (i) and (ii) for at least about 1 month. In some embodiments, the kit may comprise a set of instructions for instructing the subject on (i) consuming the first oral dosage form in daytime, (ii) consuming a combination of the first and second oral dosage forms at once in nighttime, and (c) repeating (i) and (ii) for a period of greater than 3 months.

In some embodiments, the first and second oral dosage forms may be administered as dietary supplements.

In some embodiments, the subject to be administered with the subject dosage forms may be an adult. In some embodiments, the subject may suffer from magnesium deficiency, mild cognitive impairment, short-term memory loss, long-term memory loss, Alzheimer's disease, Parkinson's disease, Huntington's disease, autism, schizophrenia, cognitive decline, depression, dementia, attention deficit hyperactivity disorder (ADHD), amyotrophic lateral sclerosis (ALS), diabetes, cardiovascular disease, hypertension, migraine, glaucoma, mood disorder, stress, anxiety, depression, sleep disorder, metabolic disorder, fatigue, cancer, HIV, hepatitis, spinal cord injury, post-surgery recovery, post-traumatic stress disorder, arthritis, neuropathic pain, inflammation, and/or tremor.

Another aspect of the invention provides a method of administering magnesium to a subject in need of supplementing magnesium. In some embodiments, at least a portion of magnesium is present in a magnesium-comprising component. In some embodiments, the method may comprise administering a first oral dosage form comprising the magnesium-comprising component. In some embodiments, the method may comprise administering a combination of (i) the first oral dosage form and (ii) a second oral dosage form comprising magnesium-comprising component. In some embodiments, the first and second oral dosage forms may exhibit different in vitro dissolution profiles in a dissolution medium. In some embodiments, the first oral dosage form and the combination of the first and second oral dosage forms may be administered at two different time points. In some embodiments, magnesium-comprising component may be present in an amount between about 200 mg to 2000 mg in each of the first and second oral dosage forms.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein) of which:

FIG. 5A shows an improvement of cognitive ability in human subjects treated with magnesium threonate, based on Mini-Mental State Examination (MMSE) analysis.

FIG. 5B shows an improvement of neuropsychiatric symptoms in human subjects treated with magnesium threonate, based on Geriatric Depression Scale (GDS) analysis.

FIG. 5C shows an improvement of neuropsychiatric symptoms in human subjects treated with magnesium threonate, based on Pittsburgh Sleep Quality Index (PSQI) analysis.

DETAILED DESCRIPTION

Figure 1A:
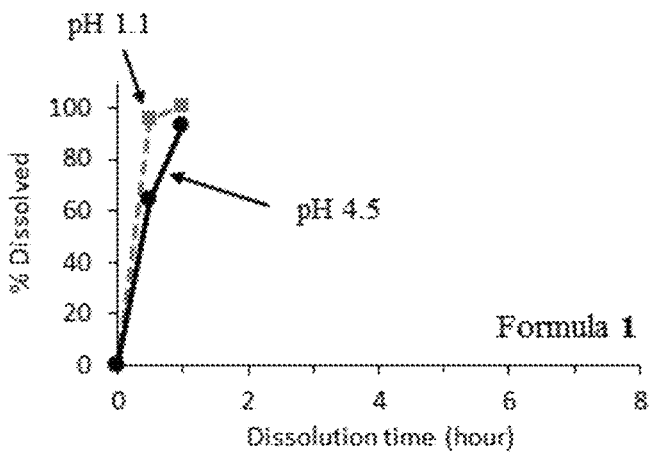
FIG. 1A shows threonic acid dissolution profiles of an immediate release oral dosage form comprising magnesium threonate when tested in two pH conditions.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Generally, the term "subject" may refer to any animal. Examples of such animals include, but are not limited to, cold-blooded animals, warm-blooded animals, mammals, domesticated mammals, primates, humans, and individuals or a patient to whom a composition is to be administered for experimental, diagnostic, nutritional, and/or therapeutic purposes. A subject or patient may be a subject or patient of normal, good, or excellent health, mood, cognitive, and/or nutritional status, or of compromised health, mood, cognitive, and/or nutritional status, including of abnormal, poor, damaged, unhealthy, impaired, diseased, and/or nutritionally deficient status. The subject may be of any age, including advanced age. The subject may be a child. The subject may be an adult.

Generally, the term "effective amount" in reference to an active agent may refer to the amount of the active agent sufficient to elicit a particular biological condition, effect, and/or response. The absolute amount of a particular agent that is effective in this manner may vary depending on various factors, such as the desired biological endpoint, the agent itself, the subject or targeted part thereof, and/or the like, for example. An effective amount of an active agent may be administered in a single dose or in multiple doses. Examples of a biological condition, effect or response that may result from an effective amount of an active agent include a maintaining and/or improving of a subject's performance of a task involving or associated with cognitive function, a maintaining and/or improving of a subject's performance in a test that measures something relating to or associated with cognitive function, a maintaining and/or improving (slowing, for example) of a rate of decline in cognitive function, and/or the like, for example. A component may be described herein as having at least an effective amount, or at least an amount effective, such as that associated with a particular goal or purpose, such as any described herein.

Generally, the term "elemental magnesium" as used in connection with a magnesium-counter ion compound described herein, may refer to a total amount of magnesium that is present as free ion and magnesium that is bound with one or more counter ions. In general, such a term is not used to refer to magnesium that may be associated with an agent other than a magnesium-counter ion compound that may be a component of a magnesium-counter ion composition (e.g., a pharmaceutical composition, a dietary supplement composition, a foodstuff supplemented with a magnesium-counter ion compound). A small amount of magnesium may be naturally present in or otherwise associated with such an agent. For example, a fruit juice extract or flavoring agent may comprise an amount of magnesium from that naturally present in the fruit from which it was derived.

Generally, the term "physiologically acceptable," or "pharmaceutically acceptable," may refer to biologically or pharmacologically compatible for in vivo use in animals or humans, e.g., approved by a regulatory agency of the Federal or a state government or listed in the U.S. Pharmacopeia or other generally recognized pharmacopeia for use in animals, and more particularly in humans.

Generally, the term "cognition" may refer to a process of obtaining, organizing, understanding, processing, and/or using information or knowledge. Generally, enhancing cognitive function refers to enhancing any aspect of such a process, such as learning, the performance of mental operations, the storage, retrieval, and/or use of information and/or thoughts, memory, and/or preventing a decline of a subject's cognitive state, for example. Various standardized tests may be used to evaluate cognition, cognitive function, and/or cognitive state and may be used to identify a subject who might be conducive to, benefit from, and/or need, maintenance and/or enhancement of same and/or to monitor an effect of treatment relating to same. Examples of suitable tests include the Mini-Mental Status Exam (Folstein, 1975), components of the PROSPER neuropsychological test battery (Houx, 2002), and/or the like. Family history, age, and/or other factors may also be used to identify a subject who might be conducive to, benefit from, and/or need, maintenance and/or enhancement of cognition, cognitive function, and/or cognitive state.

As used herein, the term "treat", in all its verb forms, included to relieve or alleviate at least one symptom of a disorder in a subject, the disorder including, e.g., pain, Alzheimer's disease, vascular dementia, or Parkinson's disease. The term "treat" may mean to relieve or alleviate the intensity and/or duration of a manifestation of a disorder experienced by a subject in response to a given stimulus (e.g., pressure, tissue injury, cold temperature, etc.). For example, in relation to dementia, the term "treat" may mean to relieve or alleviate cognitive impairment (such as impairment of memory and/or orientation) or impairment of global functioning (activities of daily living, ADL) and/or slow down or reverse the progressive deterioration in ADL or cognition. Within the meaning of the present invention, the term "treat" also denote to arrest, delay the onset (i.e., the period prior to clinical manifestation of a disease) and/or reduce the risk of developing or worsening a disease. The term "protect" is used herein to mean prevent delay or treat, or all, as appropriate, development or continuance or aggravation of a disease in a subject. Within the meaning of the present invention, the dementia is associated with a CNS disorder, including without limitation neurodegenerative diseases such as Alzheimer's disease (AD), Down's Syndrome and cerebrovascular dementia (VaD). The term "treatment" includes the act of "treating" as defined above.

A composition, kit, and/or method described herein may be useful for purposes described herein, such as maintaining, enhancing, and/or improving health, nutrition, and/or another condition of a subject, and/or cognitive, learning, and/or memory function, for example, such as magnesium deficiency, mild cognitive impairment (MCI), short-term memory loss, long-term memory loss, Alzheimer's disease (AD), Parkinson's disease (PD), Huntington's disease (HD), autism, schizophrenia, cognitive decline, depression, dementia, attention deficit hyperactivity disorder (ADHD), amyotrophic lateral sclerosis (ALS), Lou Gehrig's disease, Schizophrenia, diabetes, cardiovascular disease, hypertension, migraine, glaucoma, mood disorder, stress, anxiety, depression, sleep disorder, metabolic disorder, fatigue, cancer, HIV, hepatitis, spinal cord injury, post-surgery recovery, post-traumatic stress disorder, arthritis, neuropathic pain, inflammation, and/or tremor, merely by way of example.

In one aspect, the present invention provides a composition comprising magnesium threonate. The composition can be formulated for any route of administration, including but not limited to oral, topic, intramuscular, subcutaneous, parenteral, sublingual, mucous membrane rectal, intrathecal, and/or nasal administration, and inhalation.

In one aspect, the present invention provides a method of administering magnesium threonate to a subject in need of supplementing magnesium. The method is characterized in that at least a portion of magnesium (Mg) and threonate (T) of the magnesium threonate may be present in a salt form of $MgT_2$. The method is characterized in that two oral dosage forms exhibiting different release profiles (e.g., in vitro dissolution profiles) of magnesium threonate may be used. The method may comprise administering only one of the two oral dosage forms. The method may comprise administering a combination of the two oral dosage forms. The method may comprise two two administrations at two different time points per day, including the administration of one of the two oral dosage forms and the administration of the combination of the two oral dosage forms. Magnesium threonate may be present in an amount between about 200 mg to 2000 mg in each of the two oral dosage forms.

In some embodiments, the subject oral dosage form may comprise at least one unit dose. Each of the oral dosage form may comprise at least 1, 2, 3, 4, 5, 6, 7, 8, 9, 10 or more unit doses. When comprising two or more unit does, each unit dose may exhibit substantially the same in vitro dissolution profile in a dissolution medium. Alternatively, when comprising two or more unit does, each unit dose may exhibit different in vitro dissolution profiles in the dissolution medium.

An oral dosage form to use in a subject method typically comprises magnesium threonate. The oral dosage form may comprise an active ingredient including magnesium, threonate, or a threonate precursor. In some embodiments, the subject composition comprises a magnesium counter ion. In some embodiments, at least a portion of the magnesium (Mg) and threonate (T) is complexed in a salt form of $MgT_2$, as illustrated in the formula provided below:

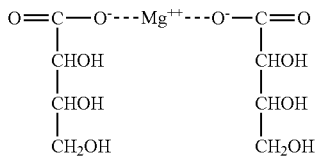

Such a composition may be prophylactically and/or therapeutically suitable or beneficial. Threonate is a natural metabolic product of vitamin C or ascorbic acid that may be associated with non-toxicity in animals (Thomas et al. 1985) and biological benefit, such as the promotion of vitamin C uptake, in animals (Verlangieri et al., 1991).

In some embodiments, the threonate comprises threonate and/or threonate precursor molecules. Threonate can be in the form of a salt. The term "threonate precursor" generally means a precursor molecule that can be readily converted to threonate when the composition is dissolved in an aqueous media or ingested as a result of ionization or hydrolysis with or without the aid of an enzyme. The precursor can be a threonic acid, an ester derivative of threonic acid or threonate, or a lactonized threonic acid. Generally, threonate as used in the present invention refers to L-threonate. For example, an L-threonate precursor may be L-threonic acid, an ester derivative of L-threonic acid or L-threonate, or a lactonized L-threonic acid. In some embodiments, D-threonate or precursors thereof are used in the present invention.

Magnesium threonate is a highly bioavailable form of a magnesium counter-ion composition. However, the in vivo accessibility of this magnesium threonate may be provided in multiple ways. In some embodiments, a subject ingests magnesium threonate. In other embodiments, magnesium may be taken with other supplements which result in an in vivo reconstitution of magnesium-counter ion composition. Without being bound by theory, the threonate may function to promote cellular uptake of magnesium in any form and may also enhance delivery to the brain and central nervous system. Thus, in some embodiments, magnesium may be given uncomplexed with threonate and threonate is provided to the same subject to enhance absorption. For example, magnesium gluconate and potassium threonate may be taken near concurrently to result in an in vivo reconstitution of magnesium threonate and/or enhance magnesium uptake and/or delivery of magnesium to the brain. In another example, certain counter ions may be metabolic products of other substances. For example, vitamin C is metabolized into the threonate ion in humans; therefore, ingestion of magnesium in a form which can be taken up by the body and vitamin C may result in the reconstitution of magnesium threonate in the body. Another example of a substance which is metabolized to threonate in humans is ascorbate. Thus, in some embodiments of the present invention, magnesium ascorbate may be provided to a subject and this substance would be metabolized to magnesium and threonate in vivo. One of skill in the art will recognize that these examples are provided by way of illustration only and that other combinations of magnesium compounds and secondary compounds may result in the reconstitution of a magnesium-counter-ion composition in vivo.

A magnesium-counter ion composition comprising more than one magnesium-counter ion compound may be suitable, beneficial or desirable relative to a magnesium-counter ion composition comprising a single magnesium-counter ion compound. A combination of more than one magnesium-counter ion compound may be suitable, beneficial or desirable in terms of any number of features or factors, such as magnesium content, solubility, palatability, magnesium bioavailability, biological acceptability, and/or the like, for example. A combination of more than one magnesium-counter ion compound may be suitable, beneficial or desirable in terms of palatability. A combination of more than one magnesium-counter ion compound may be suitable, beneficial or desirable in terms of maintaining and/or enhancing an attribute or attributes of a magnesium-counter ion compound or several magnesium-counter ion compounds.

The relative amount of threonate-to-magnesium molar ratio can be adjusted for various formulations. In some examples, the molar ratio of threonate-to-magnesium is ≥~1/5. Because each magnesium threonate ($MgT_2$) contains 2 threonate, this means at least 10% of Mg is from $MgT_2$. The other 90% may be from magnesium chloride ($MgCl_2$) or other Mg salt. In some embodiments, the threonate-to-magnesium molar ratio is ≥~2/7. In other embodiments, the threonate-to-magnesium molar ratio is about 2. In some embodiments, all threonate in said composition is in the form of magnesium threonate, which is the effective component of said compositions. When said magnesium and threonate are each part of separate compounds in the compositions and said compositions are dissolved or orally ingested, at least part of the magnesium and part of threonate will form magnesium threonate in situ as a result of ionic exchange reactions. In some embodiments, all of the magnesium and all of the threonate are from the same magnesium threonate compound, e.g., to minimize the mass of the composition. In some embodiments, when the threonate to magnesium molar ratio is less than 2, a portion of the magnesium comes from another magnesium compound. In some embodiments, the other magnesium compound is selected from magnesium chloride, magnesium taurinate, magnesium lactate, magnesium gluconate, magnesium citrate, and magnesium malate.

The exact amount of magnesium used in a given dosage form (e.g., one or more oral dosage forms) of the present invention depends on the physical form of said composition. According to one embodiment, the invention provides a solid or semi-solid composition comprising at least 1%, 2%, 3%, 4%, 5%, 6%, 7%, 8%, 9%, or 10% or more elemental magnesium by weight.

In addition to magnesium threonate, the compositions of the subject dosage form may comprise at least one magnesium-comprising component (MCC) or also used herein as magnesium-counter ion compound. Examples of an MCC include a magnesium salt of an amino acid, magnesium acetate, magnesium ascorbate, magnesium citrate, magnesium gluconate, magnesium lactate, magnesium malate, magnesium pyrrolidone carboxylate, and magnesium taurate. Alternate salts of the compositions disclosed herein include, but are not limited to, acid addition salts, such as those made with hydrochloric, methylsulfonic, hydrobromic, hydroiodic, perchloric, sulfuric, nitric, phosphoric, acetic, propionic, glycolic, lactic pyruvic, malonic, succinic, maleic, fumaric, maleic, tartaric, citric, benzoic, carbonic cinnamic, mandelic, methanesulfonic, ethanesulfonic, hydroxyethanesulfonic, benezenesulfonic, p-toluene sulfonic, cyclohexanesulfamic, salicyclic, p-aminosalicylic, 2-phenoxybenzoic, and 2-acetoxybenzoic acid. The term "salts" can also include addition salts of free acids or free bases. All of these salts (or other similar salts) may be prepared by conventional means. All such salts are acceptable provided that they are non-toxic and do not substantially interfere with the desired pharmacological activity.

A dissolution profile, i.e., the extent of release of the magnesium and/or threonic acid over a desired time, can be conveniently determined for a given time by measuring the release under controlled conditions, e.g., using a USP dissolution apparatus. Preferred release profiles are those which slow the rate of uptake of the magnesium into the blood stream while providing therapeutically effective levels of the magnesium. According to standardized dissolution testing guidelines for controlled release ("CR") profiles, dissolution of the active ingredient is measured at given intervals over a period of time. A minimum of three time points is recommended and generally cover early, middle and late stages of the dissolution profile. The last measurement should be no earlier than the time point where at least 80 percent (%) of the active ingredient is dissolved (Guidance for Industry, "Extended Release Oral Dosage Forms: Development, Evaluation, and Application of In Vitro/In Vivo Correlations", Food and Drug Administration, CDER, September 1997, Page 17). Adequate sampling is important: for example, at 1, 2 and 4 hours and every two hours thereafter until 80% of the active ingredient is released (Guidance for Industry, SUPAC-MR: Modified Release Solid Oral Dosage Forms," Food and Drug Administration, CDER, September 1997, Page 6). The preferred dissolution apparatus is USP apparatus I (basket) or II (paddle), used at recognized rotation speeds, e.g., 100 revolutions per minute (rpm for the basket and 50-75 rpm for the paddle (Guidance for Industry, "Extended Release Oral Dosage Forms: Development, Evaluation, and Application of In Vitro/In Vivo Correlations", Food and Drug Administration, CDER, September 1997, Page 4). Controlled release dosage forms permit the release of the active ingredient over an extended period of time. On the other hand, materials which dissolve at least 80% in the first 30 to 60 minutes in solution qualify as immediate release (IR) profiles. ("Dissolution Testing of Immediate Release Solid Oral Dosage Forms", issued August 1997, Section IV-A).

In some embodiments, the subject oral dosage form is a controlled release formulation. In some embodiments, the subject oral dosage form exhibits an in vitro dissolution profile in which the dissolution of threonic acid and/or magnesium ranges between about 10% to 40% in about 1 hour. In some embodiments, in about 1 h, the in vitro dissolution profile may be at least about 10%. In some embodiments, in about 1 h, the in vitro dissolution profile may be at most about 40%. In some embodiments, in about 1 h, the in vitro dissolution profile may range between about 10% to about 20%, about 10% to about 30%, about 10% to about 35%, about 10% to about 40%, about 20% to about 30%, about 20% to about 40%, or about 30% to about 40%. In some embodiments, in about 1 h, the in vitro dissolution profile may be about 10%, about 20%, about 30%, or about 40%. In some embodiments, the subject oral dose exhibits an in vitro dissolution profile in which the dissolution of threonic acid and/or magnesium ranges between about 20% to 60% in about 2 hours. In some embodiments, in about 2 h, the in vitro dissolution profile may be at least about 20%. In some embodiments, in about 2 h, the in vitro dissolution profile may be at most about 60%. In some embodiments, in about 2 h, the in vitro dissolution profile may range between about 20% to about 30%, about 20% to about 40%, about 20% to about 50%, about 20% to about 60%, about 30% to about 40%, about 30% to about 50%, about 30% to about 60%, about 40% to about 50%, about 40% to about 60%, or about 50% to about 60%. In some embodiments, in about 2 h, the in vitro dissolution profile may be about 20%, about 30%, about 40%, about 50%, or about 60%. In some embodiments, the subject oral dose exhibits an in vitro dissolution profile in which the dissolution of threonic acid and/or magnesium is greater than about 80% in about 4 hour.

In some embodiments, in about 4 h, the in vitro dissolution profile may be greater than about 85%. In some embodiments, in about 4 h, the in vitro dissolution profile may be greater than about 90%. In some embodiments, in about 4 h, the in vitro dissolution profile may be greater than about 95%. In some embodiments, the subject oral dose exhibits an in vitro dissolution profile in which the dissolution of threonic acid and/or magnesium is greater than about 90% in about 6 hours. In some embodiments, the subject oral dose exhibits an in vitro dissolution profile in which the dissolution of threonic acid and/or magnesium is greater or equal to about 95% in about 8 hour. In some embodiments, the subject oral dose exhibits an in vitro dissolution profile in which the dissolution of threonic acid and/or magnesium ranges between (i) about 10 to 40% in about 1 hour, (ii) about 20 to 60% in about 2 hours, (iii) greater than about 80% in about 4 hours, (iv) greater than about 90% in about 6 hours, and (v) greater or equal to about 95% in about 8 hour.

A controlled release magnesium composition of the present invention can adopt a number of controlled release dosage forms, which can be referred as equivalents to modified release, continuous release, delayed release, depot, gradual release, long-term release, programmed release, prolonged release, proportionate release, protracted release, repository, retard, slow release, spaced release, sustained release, time coat, timed release, delayed action, extended action, layered-time action, long acting, prolonged action, repeated action, slowing acting, sustained action, sustained-action medications, and extended release, so long as these forms exhibit the desired dissolution profile disclosed herein. Further discussions of these terms may be found in Lesczek Krowczynski, Extended-Release Dosage Forms, 1987 (CRC Press, Inc.). The various controlled release technologies cover a very broad spectrum of dosage forms. Controlled release technologies include, but are not limited to, physical systems and chemical systems.

In some embodiments, the subject oral dosage form is an immediate release formulation. In some embodiments, the subject oral dosage form exhibits an in vitro dissolution profile in which the dissolution of threonic acid and/or magnesium is greater than or equal to about 50% in about 0.5 hour. In some embodiments, in about 0.5 h, the in vitro dissolution profile may be greater than or equal to about 55%. In some embodiments, in about 0.5 h, the in vitro dissolution profile may be greater than or equal to about 60%. In some embodiments, in about 0.5 h, the in vitro dissolution profile may be greater than or equal to about 65%. In some embodiments, in about 0.5 h, the in vitro dissolution profile may be greater than or equal to about 70%. In some embodiments, in about 0.5 h, the in vitro dissolution profile may be greater than or equal to about 75%. In some embodiments, in about 0.5 h, the in vitro dissolution profile may be greater than or equal to about 80%. In some embodiments, in about 0.5 h, the in vitro dissolution profile may be greater than or equal to about 85%. In some embodiments, in about 0.5 h, the in vitro dissolution profile may be greater than or equal to about 90%. In some embodiments, the subject oral dosage form exhibits an in vitro dissolution profile in which the dissolution of threonic acid and/or magnesium is greater or equal to about 80% in about 1 hour. In some embodiments, in about 1 h, the in vitro dissolution profile may be greater than or equal to about 85%. In some embodiments, in about 1 h, the in vitro dissolution profile may be greater than or equal to about 90%. In some embodiments, in about 1 h, the in vitro dissolution profile may be greater than or equal to about 95%. In some embodiments, the subject oral dosage form exhibits an in vitro dissolution profile in which the dissolution of threonic acid and/or magnesium ranges between (i) greater than or equal to about 50% in about 0.5 hour, and (ii) greater or equal to about 80% in about 1 hour.

In some embodiments, the subject combination of two different oral dosage forms (e.g., a controlled release formulation and an immediate release formulation) exhibits an in vitro dissolution profile in which the dissolution of threonic acid and/or magnesium ranges between about 50% to about 80% in about 1 hour. In some embodiments, in about 1 h, the in vitro dissolution profile may be at least about 50%. In some embodiments, in about 1 h, the in vitro dissolution profile may be at most about 85%. In some embodiments, in about 1 h, the in vitro dissolution profile may be about 50% to about 55%, about 50% to about 60%, about 50% to about 65%, about 50% to about 70%, about 50% to about 75%, about 50% to about 80%, about 50% to about 85%, about 55% to about 60%, about 55% to about 65%, about 55% to about 70%, about 55% to about 75%, about 55% to about 80%, about 55% to about 85%, about 60% to about 65%, about 60% to about 70%, about 60% to about 75%, about 60% to about 80%, about 60% to about 85%, about 65% to about 70%, about 65% to about 75%, about 65% to about 80%, about 65% to about 85%, about 70% to about 75%, about 70% to about 80%, about 70% to about 85%, about 75% to about 80%, about 75% to about 85%, or about 80% to about 85%. In some embodiments, in about 1 h, the in vitro dissolution profile may be about 50%, about 55%, about 60%, about 65%, about 70%, about 75%, about 80%, or about 85%. In some embodiments, the subject combination of two different oral dosage forms exhibits an in vitro dissolution profile in which the dissolution of threonic acid and/or magnesium is greater than about 60% in about 2 hours. In some embodiments, in about 2 h, the in vitro dissolution profile may be greater than or equal to about 65%. In some embodiments, in about 2 h, the in vitro dissolution profile may be greater than or equal to about 70%. In some embodiments, in about 2 h, the in vitro dissolution profile may be greater than or equal to about 75%. In some embodiments, in about 2 h, the in vitro dissolution profile may be greater than or equal to about 80%. In some embodiments, in about 2 h, the in vitro dissolution profile may be greater than or equal to about 90%. In some embodiments, the subject combination of two different oral dosage forms exhibits an in vitro dissolution profile in which the dissolution of threonic acid and/or magnesium is greater than about 80% in about 4 hours. In some embodiments, in about 4 h, the in vitro dissolution profile may be greater than or equal to about 85%. In some embodiments, in about 4 h, the in vitro dissolution profile may be greater than or equal to about 90%. In some embodiments, in about 4 h, the in vitro dissolution profile may be greater than or equal to about 95%. In some embodiments, the subject combination of two different oral dosage forms exhibits an in vitro dissolution profile in which the dissolution of threonic acid and/or magnesium ranges between (i) about 50% to 75% in about 1 hour, (ii) greater than about 60% in about 2 hours, and (iii) greater than about 80% in about 4 hours.

In some embodiments, the subject oral dosage form may comprise magnesium threonate in an amount of about 200 mg to about 2,000 mg. In some embodiments, the subject oral dosage form may comprise magnesium threonate in an amount of at least about 200 mg. In some embodiments, the subject oral dosage form may comprise magnesium threonate in an amount of at most about 2,000 mg. In some embodiments, the subject oral dosage form may comprise magnesium threonate in an amount of about 200 mg to about 300 mg, about 200 mg to about 400 mg, about 200 mg to about 500 mg, about 200 mg to about 600 mg, about 200 mg to about 800 mg, about 200 mg to about 1,000 mg, about 200 mg to about 1,200 mg, about 200 mg to about 1,400 mg, about 200 mg to about 1,600 mg, about 200 mg to about 1,800 mg, about 200 mg to about 2,000 mg, about 300 mg to about 400 mg, about 300 mg to about 500 mg, about 300 mg to about 600 mg, about 300 mg to about 800 mg, about 300 mg to about 1,000 mg, about 300 mg to about 1,200 mg, about 300 mg to about 1,400 mg, about 300 mg to about 1,600 mg, about 300 mg to about 1,800 mg, about 300 mg to about 2,000 mg, about 400 mg to about 500 mg, about 400 mg to about 600 mg, about 400 mg to about 800 mg, about 400 mg to about 1,000 mg, about 400 mg to about 1,200 mg, about 400 mg to about 1,400 mg, about 400 mg to about 1,600 mg, about 400 mg to about 1,800 mg, about 400 mg to about 2,000 mg, about 500 mg to about 600 mg, about 500 mg to about 800 mg, about 500 mg to about 1,000 mg, about 500 mg to about 1,200 mg, about 500 mg to about 1,400 mg, about 500 mg to about 1,600 mg, about 500 mg to about 1,800 mg, about 500 mg to about 2,000 mg, about 600 mg to about 800 mg, about 600 mg to about 1,000 mg, about 600 mg to about 1,200 mg, about 600 mg to about 1,400 mg, about 600 mg to about 1,600 mg, about 600 mg to about 1,800 mg, about 600 mg to about 2,000 mg, about 800 mg to about 1,000 mg, about 800 mg to about 1,200 mg, about 800 mg to about 1,400 mg, about 800 mg to about 1,600 mg, about 800 mg to about 1,800 mg, about 800 mg to about 2,000 mg, about 1,000 mg to about 1,200 mg, about 1,000 mg to about 1,400 mg, about 1,000 mg to about 1,600 mg, about 1,000 mg to about 1,800 mg, about 1,000 mg to about 2,000 mg, about 1,200 mg to about 1,400 mg, about 1,200 mg to about 1,600 mg, about 1,200 mg to about 1,800 mg, about 1,200 mg to about 2,000 mg, about 1,400 mg to about 1,600 mg, about 1,400 mg to about 1,800 mg, about 1,400 mg to about 2,000 mg, about 1,600 mg to about 1,800 mg, about 1,600 mg to about 2,000 mg, or about 1,800 mg to about 2,000 mg. In some embodiments, the subject oral dosage form may comprise magnesium threonate in an amount of about 200 mg, about 300 mg, about 400 mg, about 500 mg, about 600 mg, about 800 mg, about 1,000 mg, about 1,200 mg, about 1,400 mg, about 1,600 mg, about 1,800 mg, or about 2,000 mg.

In some embodiments, the subject oral dosage form may comprise magnesium-comprising compound (MCC) in an amount of about 200 mg to about 2,000 mg. In some embodiments, the subject oral dosage form may comprise magnesium-comprising compound (MCC) in an amount of at least about 200 mg. In some embodiments, the subject oral dosage form may comprise magnesium-comprising compound (MCC) in an amount of at most about 2,000 mg. In some embodiments, the subject oral dosage form may comprise magnesium-comprising compound (MCC) in an amount of about 200 mg to about 400 mg, about 200 mg to about 600 mg, about 200 mg to about 800 mg, about 200 mg to about 1,000 mg, about 200 mg to about 1,500 mg, about 200 mg to about 2,000 mg, about 400 mg to about 600 mg, about 400 mg to about 800 mg, about 400 mg to about 1,000 mg, about 400 mg to about 1,500 mg, about 400 mg to about 2,000 mg, about 600 mg to about 800 mg, about 600 mg to about 1,000 mg, about 600 mg to about 1,500 mg, about 600 mg to about 2,000 mg, about 800 mg to about 1,000 mg, about 800 mg to about 1,500 mg, about 800 mg to about 2,000 mg, about 1,000 mg to about 1,500 mg, about 1,000 mg to about 2,000 mg, or about 1,500 mg to about 2,000 mg. In some embodiments, the subject oral dosage form may comprise magnesium-comprising compound (MCC) in an amount of about 200 mg, about 400 mg, about 600 mg, about 800 mg, about 1,000 mg, about 1,500 mg, or about 2,000 mg.

An example of an immediate release tablet formulation (Formula 1) is shown in Example 1 and Table 2. The Formula 1 tablet comprises magnesium L-threonate as magnesium composition, povidone K-90 binder, microcrystalline cellulose as glidant, colloidal silicon dioxide as filler, polyplasdone as disintegrant, magnesium stearate lubricant, and talc as inert powders. The in vitro dissolution profiles of Formula 1 in pH 1.1 and 4.5 are shown in Table 3 and FIG. 1A. For Formula 1, the release profile of threonic acid, which may be substantially equivalent to the release profile of magnesium, ranges between (i) greater than or equal to about 50% in 0.5 hour and (ii) greater than or equal to about 80% in about an hour as measured using a USP type II (paddle) dissolution system at 75 rpm, at a temperature of about 37° C., in pH 1.1 and 4.5.

Figure 1B:
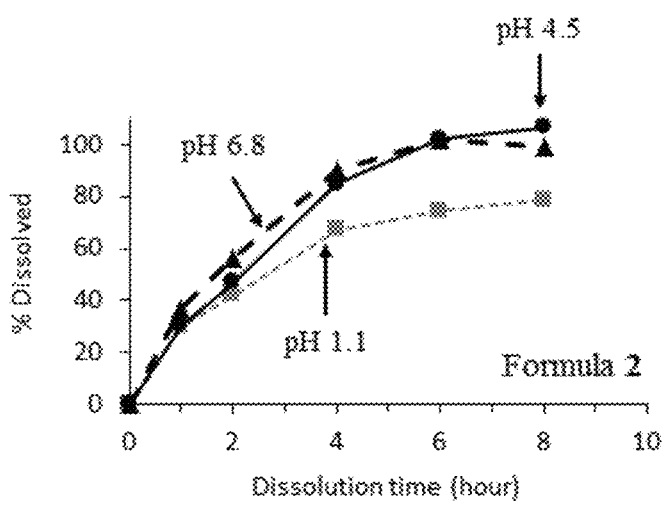
FIG. 1B shows threonic acid dissolution profiles of a controlled release oral dosage form comprising magnesium threonate when tested in three pH conditions.

An example of a controlled release tablet formulation (Formula 2) is shown in Example 2 and Table 4. The Formula 2 tablet comprises magnesium L-threonate as magnesium composition, providone K-90 as binder, microcrystalline cellulose as glidant, colloidal silicon dioxide as filler, carbopol and carboxyl methyl cellulose as swellable materials, Starcap starch, magnesium stearate lubricant, and talc as inert powders. The in vitro dissolution profiles of Formula 2 in pH 1.1, 4.5 and 6.8 are shown in Table 5 and FIG. 1B. For Formula 2, the release profile of threonic acid, which may be substantially equivalent to the release profile of magnesium, ranges between (i) about 10% to 35% in about 1 hour, (ii) about 20% to 50% in about 2 hours, (iii) greater than about 80% in about 4 hours, (iv) greater than about 90% in about 6 hours, and (v) greater than or equal to about 95% in about 8 hours as measured using a USP type II (paddle) dissolution system at 75 rpm, at a temperature of about 37° C., in pH 4.5 and 6.8.

Figure 1C:
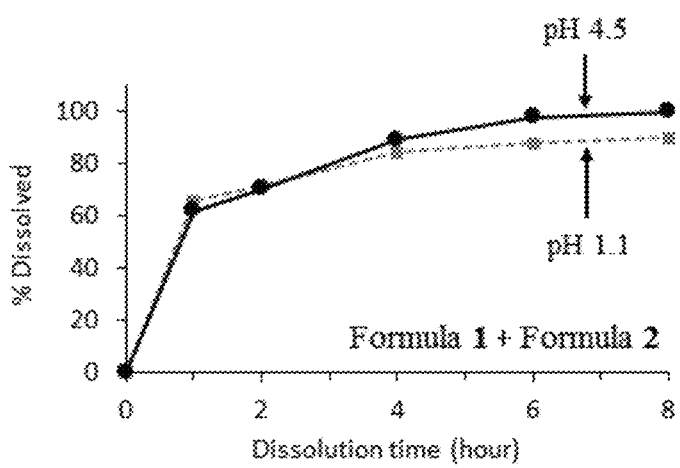
FIG. 1C shows threonic acid dissolution profiles of a combination of the immediate release and the controlled release oral dosage forms comprising magnesium threonate when tested in two pH conditions.

In some embodiments, two different oral dosage forms of magnesium threonate may be used for a single administration of magnesium threonate. Each of the two oral dosage forms may exhibit different in vitro dissolution profiles in the same dissolution medium. In an example, a combination of the immediate release tablet (Formula 1) and the controlled release tablet (Formula 2) may be used as a single administration of magnesium threonate. An example of a combination of the immediate release tablet (Formula 1) and the controlled release tablet (Formula 2), and the resulting in vitro dissolution profiles in pH 1.1 and 4.5 are shown in Example 3, Table 6, and FIG. 1C. For the combination of Formula 1 and Formula 2, the release profile of threonic acid, which may be substantially equivalent to the release profile of magnesium, ranges between (i) about 50% to 75% in about 1 hour, (ii) greater than about 60% in about 2 hours, and (iii) greater than about 80% in about 4 hours as measured using a USP type II (paddle) dissolution system at 75 rpm, at a temperature of about 37° C., in pH 1.1 and 4.5.

The present invention provides methods of using the compositions disclosed herein. In some embodiments, such uses comprise administering the oral dosage forms of the present invention to provide a variety of health benefits. Such a composition may comprise at least one magnesium-counter ion compound. A magnesium-counter ion (e.g., magnesium threonate) composition described herein may be useful for any of a variety of applications and purposes described herein, such as maintaining, enhancing, and/or improving health, nutrition, and/or another condition of a subject, and/or cognitive, learning, and/or memory function, for example. Magnesium deficit may lead to or may be associated with many pathological symptoms, such as loss of appetite, nausea, vomiting, fatigue, seizures, abnormal heart rhythms, diabetes, and/or cardiovascular disease, for example. According to several studies, magnesium deficit may lead to or may be associated with attention deficit hyperactivity disorder (ADHD) in children and symptoms associated therewith (Kozielec et al., 2006). A magnesium-counter ion composition described herein may be useful for administration to a subject presenting magnesium deficiency, mild cognitive impairment, Alzheimer's disease, attention deficit hyperactivity disorder, ALS, Parkinson's disease, diabetes, migraine, anxiety disorder, mood disorder, hypertension, cancer, HIV, hepatitis, spinal cord injury, post-surgery recovery, post-traumatic stress disorder, arthritis, neuropathic pain, inflammation, and/or tremor merely by way of example.

Not wishing to be bound by theory, a magnesium-counter ion and/or a method described herein may be useful for regulating cortical neuronal excitability. For neurological function, regulation of cortical neuronal excitability ("neuronal excitability" or "cortical excitability") may be critical (Badawy et al., 2012). As a complex cellular network the nervous system may be composed of as many as 10 billion neurons and 60 trillion synapses that mediate interneuronal communication. Each neuron may be regarded as a component in a complex system of highly specialized, distinct neural circuits. Every aspect of behavior, from primitive reflexes to abstract thinking and emotion, may rely on the precision of the computational processes performed by these circuits, which in turn may critically dependent on healthy excitatory and inhibitory systems. These systems may be facilitated by the interaction of neurotransmitters and cellular receptors to determine the level of neuronal excitability (excited or inhibited) either directly by controlling flow of ions through ion channels or through a complex cascade of intracellular interactions via secondary messengers. Examples of neurotransmitters include adrenaline, noradrenaline, dopamine, serotonin, gamma-aminobutyric acid (GABA), acetylcholine, glutamate, and endorphin. In some examples, excitation may be facilitated by the action of glutamate on N-methyl-d-aspartate (NMDA), and non-NMDA receptors. In some examples, inhibition may be mediated by the action of GABA on GABAA and GABAB receptors. The patterns of interneuronal connections and communication may not be permanent, but instead show variability and reorganization. Thus, cortical excitability may play a critical role in growth and development, learning and memory. On the other hand, alterations or uncontrolled cortical excitability, as well as abnormal reorganization of brain circuits may result in disturbed function and manifest as various neurological disorders (e.g., epilepsy, stroke, amyotrophic lateral sclerosis (ALS), dementia, migraine, dystonia, Parkinson's disease (PD), Huntington's disease (HD), tremor, etc.).

Cortical excitability may be regulated daily. For example, the excitability in the frontal cortex increases during the time that one is awake and is reset to a low state during sleep (Huber et al., 2013; Gorgoni et al., 2014). In healthy humans, high cortical excitability may be associated with poor cognitive ability. For example, frontal cortical excitability is inversely correlated with attention (Ly et al., 2016). Elevated cortical excitability during nighttime can prevent a person from entering slow wave sleep (SWS) and maintaining good sleep, resulting in more wake after sleep onset (WASO) and reduced degree of refreshment following arousal.

During aging and in neurodegenerative disease, cortical excitability may be elevated significantly. In aging, there may be a reduction of cortical inhibition and elevation of cortical excitability (Oliviero et al., 2006), leading to reduced cognitive function. Patients suffering from neurodegenerative disease, such as mild cognitive impairment (MCI), may exhibit increased cortical neuronal excitability (Olazanin et al., 2010). The largest change in cortical excitability may occur in Alzheimer's disease (AD) patients, in which case cortical excitability may be significantly lower than that in cognitively normal controls (Di Lazzaro, 2004; Khedr et al., 2011).

Neuronal excitability may be determined by assessing (i) individual excitatory and/or inhibitory synapses on a neuron and (ii) intrinsic neuronal excitability. Not wishing to be bound by theory, daily fluctuation of neuronal excitability may be most likely due to a change of a probability of transmitter release (Pr), which is constantly regulated by circulating hormones and neurotransmitters. Additionally, the capacity of a synaptic network may be determined by the capacity of individual synapses and the total number of functional synapses within the network (i.e., functional synapse density). An inverse relationship may exist between Pr and the functional synapse density—the higher the Pr of individual synapses, the lower the density of functional synapses. Such inverse relationship between Pr and the functional synapse density may result in a homeostatic regulation of total synaptic input. In some examples, a gradual increase of cortical excitability via upregulation of Pr throughout the day is associated with a reduction of functional synapse density, resulting in a reduction of cognitive ability.

Sleep may be important for reducing the Pr of individual synapses and restoring the functional synapse density. A full night sleep may adjust Pr to its lowest level and the functional synapse density to its highest level to prepare for a new day of synaptic function. A number of molecules may regulate sleep, thereby regulating cortical excitability. Not wishing to be bound by theory, elevation of cortical excitability in elderly and in individuals with neurological disorders (e.g., Alzheimer's disease (AD)) may be caused by multiple factors, including decreased levels of growth hormone (GH) and melatonin, increased level of cortisol, and decreased amyloid beta clearance (e.g., increased amyloid beta production and/or deposition) during nighttime.

Amyloid beta (Amyloid-β or Abeta) release may be regulated by neuronal activity (Cirrito et al., 2008; Cirrito et al., 2005). In humans, the concentration of amyloid beta may be determined by the balance of the amyloid beta production rate and its clearance rate (Bateman et al., 2006). Amyloid beta may have a diurnal variation. The concentration of amyloid beta may decrease during sleep, with the lowest level occurring in the morning (Ooms et al., 2014). Reduction of amyloid beta levels during sleep may be due to an increase in amyloid-β clearance rate. Not wishing to be bound by theory, this may be due to an increase in the interstitial space volume during periods of sleep, resulting in higher cerebral spinal fluid (CSF) flow through the dilated interstitial space (Xie et al., 2013).

Figure 2A:
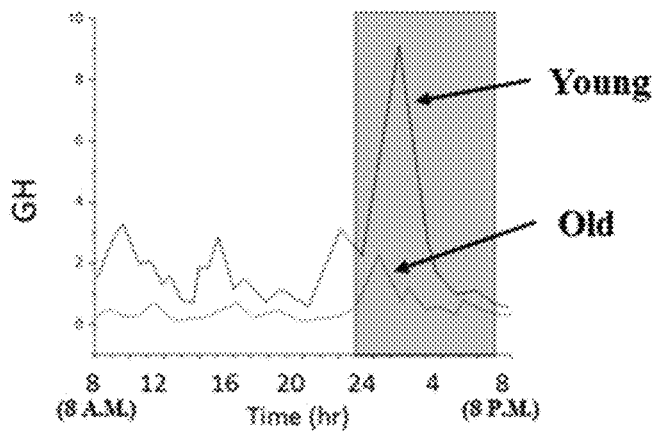
FIG. 2A shows model expression profiles of growth hormone (GH) in young adults and old adults, over the course of one day (24 hours).
Figure 2B:
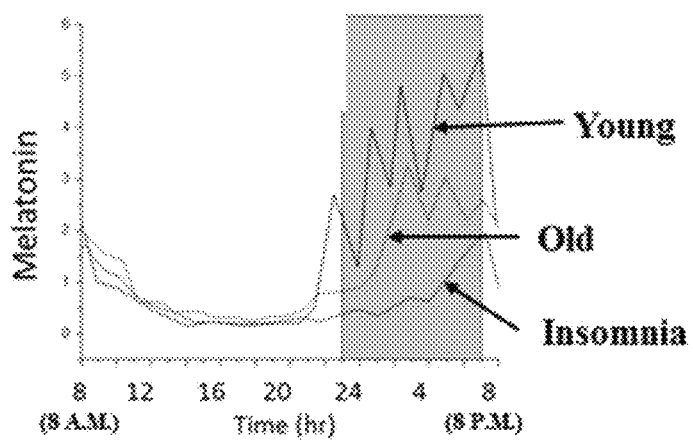
FIG. 2B shows model expression profiles of melatonin in young adults, old adults, and patients with insomnia, over the course of one day (24 hours).
Figure 2C:
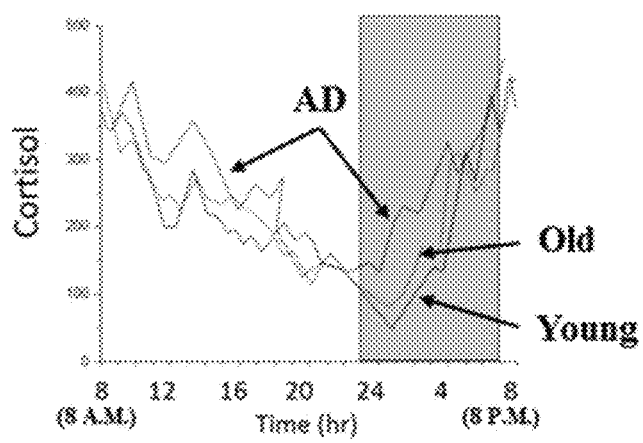
FIG. 2C shows model expression profiles of cortisol in patients with Alzheimer's disease (AD), over the course of one day (24 hours).

Hormones (or signaling molecules) and their expression profiles throughout the day may regulate wakefulness and sleep. Not wishing to be bound by theory, an improper expression of hormones in the elderly may lead to a poor sleep, increased probability of transmitter release (Pr), increased cortical excitability, and ultimately reduced cognitive function on the following day. FIG. 2A-C show illustrative circadian rhythm of hormones in plasma (e.g., growth hormone (GH), melatonin, cortisol, etc) that regulate wakefulness and sleep in young and old human adults, and humans in disease states. Expression profiles of the hormones throughout the course of 24 hours are shown from 8 A.M. on the first day to 8 A.M on the second day, and gray area in each graph denotes a typical sleep time range. In these examples, GH may exert inhibitory effects on cortical excitability, wherein cortisol may exert stimulatory effects on cortical excitability. In daytime, a high concentration of cortisol and low concentrations of GF and melatonin may result in an overall high cortical excitability that is suitable for daytime cognitive function. On the other hand, in nighttime, opposite trends in the expression of the plasma hormones may result in an overall low cortical excitability that is suitable for promoting sleep.

FIG. 2A shows illustrative circadian rhythm of GH in young adults, exhibiting the fluctuation of GH expression throughout the day and a spike of GH expression during nighttime sleep (approximately midnight to 2 A.M.). On the other hand, old adults may have significantly lower GH concentration in nighttime (Van Cauter et al., 2000). Not wishing to be bound by theory, magnesium may be related to expression of GH (e.g., aiding in the production of GH), and the administration of magnesium may improve sleep and cognitive function in the aged adults. FIG. 2B shows illustrative fluctuation of melatonin plasma concentrations throughout the day, peaking during the nighttime sleep. The melatonin concentration may be the highest during sleep for young adults. On the other hand, the melatonin concentration in old adults may be about half the concentration of young adults, and the melatonin concentration in patients with insomnia may be significantly lower than both young and old adults without insomnia (Haimov et al., 1994). Not wishing to be bound by theory, magnesium may be related to expression of melatonin (e.g., enhance the formation of melatonin from serotonin (Peuhkuri et al., 2012)), and the administration of magnesium may improve sleep and cognitive function in the aged adults and individuals suffering from neurological disorders and/or insomnia. FIG. 2C shows illustrative fluctuation of cortisol plasma concentration throughout the day, peaking during early morning. While the cortisol plasma concentrations in young and old adults may be relatively the same throughout the day (Van Cauter et al., 1996), patients with AD may have a significant increase during nighttime (Hartmann A Neurobiology 1997). Not wishing to be bound by theory, magnesium may modulate cortisol expression and amyloid-beta protein precursor trafficking and processing, and the administration of magnesium may improve sleep and cognitive function in individuals suffering from neurological disorders.

Figure 3A:
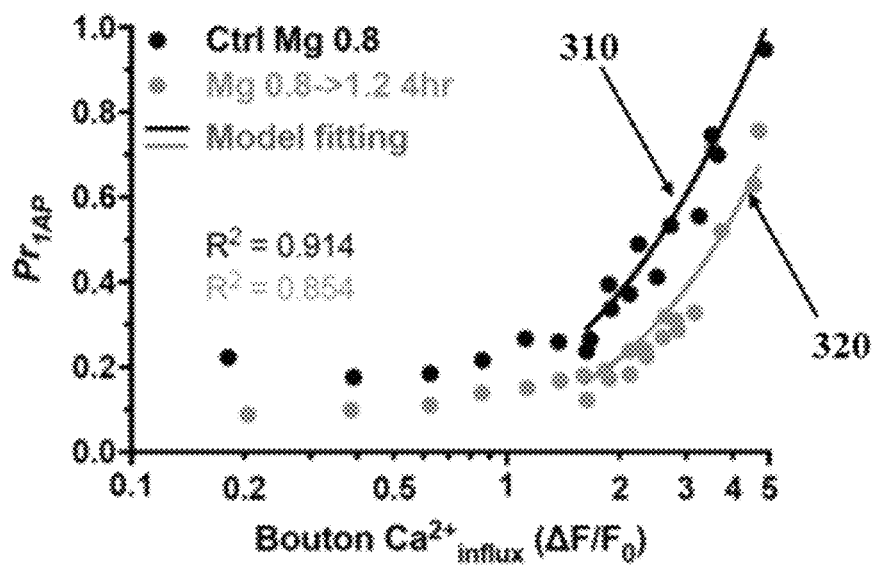
FIG. 3A shows the effect of an increase in magnesium concentration on the probability of transmitter release (Pr) of neuronal cells at varying calcium concentrations.
Figure 3B:
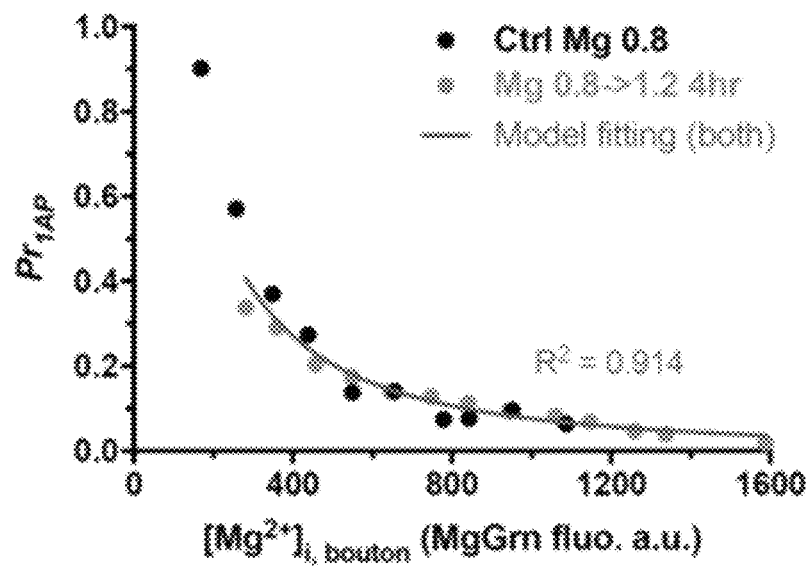
FIG. 3B shows the effect of an increase in magnesium concentration on the probability of transmitter release (Pr) of neuronal cells at a low intracellular calcium concentration.

An example of the effect of calcium and magnesium on the regulation of Probability of transmitter release (Pr) is shown in FIG. 3. In an experiment, rat hippocampal neurons were cultured in vitro in varying concentrations of extracellular calcium or magnesium, thereby effectively varying concentrations of intracellular calcium or magnesium. A traceable dye was used as a model neurotransmitter to measure the change in Pr. There was a strong positive correlation between increasing intracellular calcium concentration and the upregulation of Pr, as shown in FIG. 3A, plot 310. Interestingly, an elevation of intracellular magnesium (induced by an increase of extracellular magnesium concentration from 0.8 millimolar (mM) to 1.2 mM for 4 h) shifted the calcium-Pr relationship to the right, as shown in FIG. 3A, plot 320. Not wishing to be bound by theory, this may suggest an inhibitory effect of magnesium on Pr. Furthermore, at a relatively low intracellular calcium concentration, the inverse relationship between intracellular magnesium concentration and Pr was more apparent, as shown in FIG. 3B. At a low calcium concentration condition, increasing the extracellular magnesium concentration promoted more synapses with a higher intracellular magnesium concentrations and low Pr values. Not wishing to be bound by theory, Pr of a central nervous system (CNS) synapse may be reciprocally regulated by intracellular magnesium and calcium.

Figures 4A, 4B, 4C:
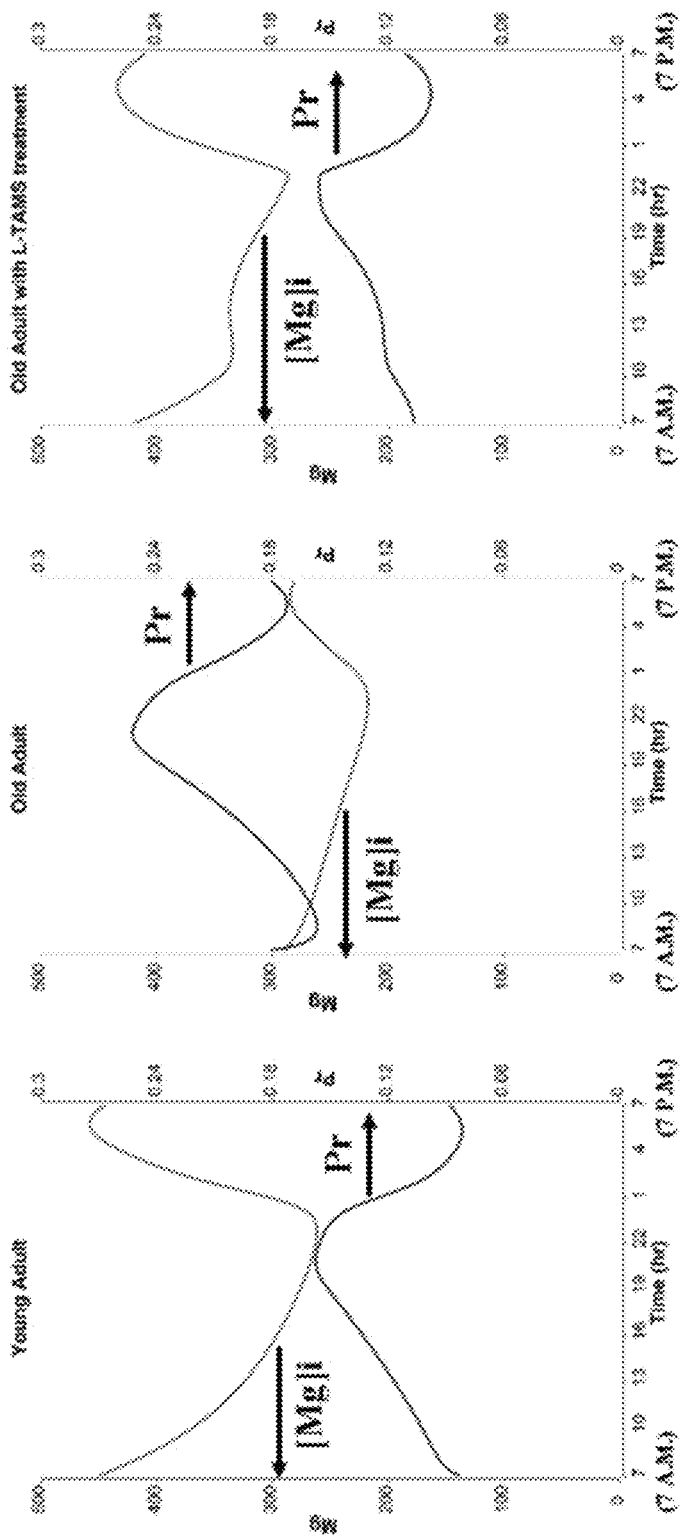
FIG. 4A shows model daily fluctuations of intracellular magnesium concentration and probability of transmitter release in a young adult.
FIG. 4B shows model daily fluctuations of intracellular magnesium concentration and probability of transmitter release in an old adult.
FIG. 4C shows model daily fluctuations of intracellular magnesium concentration and probability of transmitter release in an old adult with magnesium threonate treatment.

Not wishing to be bound by theory, the daily fluctuation of the probability of transmitter release (Pr), and thus the daily fluctuation of cortical excitability, may be predicted by the daily fluctuation of a number of circadian rhythm signaling molecules (e.g., GH, melatonin, cortisol, etc.). As such, the daily fluctuations of the signaling molecules may be incorporated to generate a model fluctuation of Pr in a young adult (FIG. 4A) and an old adult (FIG. 4B). In addition, some of the signaling molecules (e.g., GH and melatonin) may activate intracellular signaling pathways and elevate intracellular magnesium (Randi-Perumal et al., 2008; Takaya et al., Torres et al., 1998; Torres et al., 2006). Thus, not wishing to be bound by theory, the daily fluctuations of such appropriate signaling molecules may be incorporated to generate a model fluctuation of intracellular magnesium concentration ([Mg]i) in a young adult (FIG. 4A) and an old adult (FIG. 4B). Not wishing to be bound by theory, Pr and cortical excitability may be elevated in an old adult, particularly in AD patients, and such elevation of cortical excitability may be one of the causes of cognitive impairment and mood disorder (Khedr et al., 2011; List et al., 2013; Ly et al., 2016). Not wishing to be bound by theory, the inverse relationship between Pr/cortical excitability and [Mg]I shown in FIGS. 4A and 4B may indicate that increasing [Mg]i in the synaptic terminal of neuronal cells may be a therapeutic avenue to reduce Pr, reduce cortical excitability, and ultimately counteract age and disease-related cortical dysfunction (FIG. 4C). Not wishing to be bound by theory, administration of magnesium threonate may thereby increase the magnesium concentration in the brain and counteract age and disease-related cognitive conditions. In some examples, different oral dosage forms comprising magnesium threonate and exhibiting different dissolution profiles may be combined to create a regimen that approximately matches the complex fluctuation profile of [Mg]i in a young adult (FIG. 4A). Not wishing to be bound by theory, administration of such regimen by the elderly may restore their Pr and cortical excitability profile to that of a young adult (FIG. 4C). Not wishing to be bound by theory, as neuronal excitability may be vary throughout the day, a daily regimen of magnesium threonate via two different formulations—with two different dissolution profiles—at two different time points may be useful.

The subject oral dosage forms comprising magnesium and/or the regimen comprised of the oral dosage forms may provide a variety of additional health benefits. Magnesium is an essential mineral in the human body and plays a role in numerous physiological functions. Yet, it is generally recognized that at least half of the people in the industrialized world do not get sufficient magnesium from their diets. Several diseases, such as diabetes and Alzheimer's disease (AD), are associated with magnesium deficit. Therefore, there is a need for magnesium supplementation. Not wishing to be bound by theory, the subject oral dosage forms and/or the regimen thereof may be administered as magnesium supplements or therapies. Not wishing to be bound by theory, the subject oral dosage forms may comprise a number of magnesium compounds, including, but are not limited to, magnesium oxide, magnesium citrate, magnesium sulfate, magnesium chloride, magnesium gluconate, magnesium lactate, magnesium pidolate and magnesium diglycinate.

In addition, magnesium supplements have been used for treating type 2 diabetes. In one study, diabetic patients were treated with nearly 1 g of magnesium daily using magnesium oxide for 1 month (de Lordes Lima, et al., *Diabetes Care*. 21: 682-6 (1998)). The treatment increased the serum magnesium level of the patients by about 10% but with only minor improvement in metabolic control. In another study, diabetic patients were treated with 720 mg/day of magnesium for three months. Similarly, the blood magnesium levels of the patients were raised by about 10% on average (Eibl, et al., *Diabetes Care*. 21: 2031-2 (1995)). However, the metabolic control of the patients, as assessed by their HbA1c levels, had no improvement. Not wishing to be bound by theory, the subject oral dosage forms and/or the regimen thereof may improve the metabolic control of subjects suffering from diabetes.

Magnesium ion has been reported to be generally useful for treatment of dementia (e.g., U.S. Pat. No. 4,985,256, entitled "Methods for diagnosing, monitoring and controlling the onset and progression of certain dementias and impeding memory loss or improving impairment of memory"). Landfield and Morgan showed that young (9-month old) and aged (25-month old) rats fed food containing 2% magnesium oxide for 8 days had shown some sign of improvement of cognitive function (Landfield and Morgan, Brain Research, 322:167-171 (1984)). However, the gain in cognitive function was transient and at the cost of diarrhea and weight loss to the animals. In fact, the side-effect was so severe the researchers had to use an alternating feeding schedule by having the animals on the high Mg diet for 4 days, followed by a regular diet for two days and then back to the high Mg diet for another 4 days. Not wishing to be bound by theory, the subject oral dosage forms and/or the regimen thereof may improve cognitive function without such side-effects in subjects suffering from dementia.

Magnesium compounds may also be used to affect bone density. Bone density disorders, including but not limited to osteoporosis, may be treated by supplementation with magnesium compounds of the present invention. Subjects may be treated to ameliorate the effects of low bone density or as prophylaxis against lost bone density. Bone density may be measured by any means known in the art, including, but not limited to, dual energy X-ray absorptiometry (DEXA), ultrasound, quantitative computed tomography, single energy absorptiometry, magnetic resonance imaging, measuring metacarpal width, and hand X-ray analysis.

In some embodiments, a daily regimen of magnesium threonate via two different oral formulations at two different time points may be provided. In some embodiments, one or both of the oral formulations may comprise of only one oral dosage form. The oral dosage form may exhibit an immediate release or a controlled release of magnesium threonate in a dissolution medium. In some embodiments, one or both of the oral formulations may comprise two oral dosage forms that exhibit different dissolution profiles of magnesium threonate (e.g., immediate and controlled release). In some embodiments, the two different time points may be daytime and nighttime. In some embodiments, the first time point administration of magnesium threonate and the second time point administration of magnesium threonate may have substantially the same amount of magnesium threonate (e.g., by weight). In some embodiments, the two different time points may be daytime and nighttime. In some embodiments, the first time point administration of magnesium threonate and the second time point administration of magnesium threonate may have different total amounts of magnesium threonate (e.g., by weight). In some embodiments, the first time point administration may have more magnesium threonate by weight than the nighttime administration. In some embodiments, the second time point administration may have less magnesium threonate by weight than the nighttime administration.

In some embodiments, the method of administering magnesium threonate to a subject comprises (a) administering, at a first time point, a first oral dosage form exhibiting a first dissolution profile of magnesium threonate, and (b) administering, at a second time point, a combination of the first oral dosage form and a second oral dosage form exhibiting a second dissolution profile of magnesium threonate. In some embodiments, the first dissolution profile of the first oral dosage form (e.g., a controlled release formulation) may be slower than a second in vitro dissolution profile of the second oral dosage form (e.g., an immediate release formulation). In some embodiments, the first dissolution profile of the first oral dosage form may be faster than a second in vitro dissolution profile of the second oral dosage form.

In some embodiments, the administration of the first oral dosage form and the administration of the combination of the first and second oral dosage forms may be separated by about 6 to 12 hours (h). In some embodiments, the administration of the first oral dosage form and the administration of the combination of the first and second oral dosage forms may be separated by about 6 h to about 12 h. In some embodiments, the administration of the first oral dosage form and the administration of the combination of the first and second oral dosage forms may be separated by at least about 6 h. In some embodiments, the administration of the first oral dosage form and the administration of the combination of the first and second oral dosage forms may be separated by at most about 12 h. In some embodiments, the administration of the first oral dosage form and the administration of the combination of the first and second oral dosage forms may be separated by about 6 h to about 7 h, about 6 h to about 8 h, about 6 h to about 9 h, about 6 h to about 10 h, about 6 h to about 11 h, about 6 h to about 12 h, about 7 h to about 8 h, about 7 h to about 9 h, about 7 h to about 10 h, about 7 h to about 11 h, about 7 h to about 12 h, about 8 h to about 9 h, about 8 h to about 10 h, about 8 h to about 11 h, about 8 h to about 12 h, about 9 h to about 10 h, about 9 h to about 11 h, about 9 h to about 12 h, about 10 h to about 11 h, about 10 h to about 12 h, or about 11 h to about 12 h. In some embodiments, the administration of the first oral dosage form and the administration of the combination of the first and second oral dosage forms may be separated by about 6 h, about 7 h, about 8 h, about 9 h, about 10 h, about 11 h, or about 12 h.

In an aspect, the present invention provides a regimen of magnesium threonate comprising the administration of the first oral dosage form and the administration of the combination of the first and second oral dosage forms per day. In some embodiments, the regimen of the two different administrations per day may be repeated for at least about 15 days. In some embodiments, the regimen of the two different administrations per day may be repeated for at least about 15, 16, 17, 18, 19, 20, 21, 22, 23, 24, 25 days or longer. In some embodiments, the regimen of the two different administrations per day may be repeated once a week, twice a week, three times a week, four times a week, five times a week, six times a week, or seven times a week. In some embodiments, the regimen of the two different administrations per day may be repeated once per month, twice per month, three times per month, four times per month, five times per month, six times per month, seven times per month, 8 times per month, 9 times per month, 10 times per month, or more. In some embodiments, the regimen of the two different administrations per day may be repeated for at least about 1 month, about 2 months, about 3 months, about 4 months, about 5 months, about 6 months, or longer. In some embodiments, the regimen of the two different administrations per day may be in a continuous manner over a lifetime.

In some embodiments, the method of administering magnesium threonate to the subject in need of supplementing magnesium may include administrate magnesium in at least an amount to improve a Mini-Mental State Examination (MMSE) score of the subject. The MMSE score may be used as an indication of the subject's cognitive function. In some embodiments, the MMSE score of the subject prior to and subsequent to starting the regimen of the two different administrations of magnesium threonate may be determined. In an experiment, fifteen patients with a clinical diagnosis of mild-to-moderate Alzheimer's disease (AD) were treated with magnesium L-threonate administration for 8 weeks. The daily dosage of magnesium L-threonate was 1800 mg as follows: (i) a controlled release oral dosage form of magnesium L-threonate (600 mg) in the morning, and (ii) a combination of the controlled release oral dosage form (600 mg) and an immediate release oral dosage form (600 mg) in the evening. The MMSE scores of the subjects were obtained at prior to treatment (T1), 8 weeks (T2) and 4 months (T3). The results show that the treatment of magnesium L-threonate administration promoted improvement in the mean MMSE score by 1.73 points (p=0.035) (FIG. 5A). In some embodiments, administering magnesium threonate may increase a subject's MMSE score by about at least 0.5, 1, 1.5, 2, 2.5, 3, 3.5, 4, 4.5, 5, 6, 7, 8, 9, 10, 11, 12, 13, 14, 15 or more points. In some embodiments, administering magnesium threonate may reduce the rate of the decrease of a subject's MMSE score by about 5%, 10%, 15%, 20%, 25%, 30%, 35%, 40%, 45%, 50%, 60%, 70%, 80%, 90%, 100% or more relative to a decrease in the historical or untreated controls. The effect of MMSE on neuropsychiatric symptoms was also tested in this study. Specifically, anxiety, depression, and sleep disorder were tested. For anxiety, there was a significant reduction in anxiety as determined by Hamilton-Anxiety (HAM-A) questionnaire (−4.22±2.54 SD; p=0.001). Not wishing to be bound by theory, magnesium and/or magnesium L-threonate administration may be used to treat anxiety. To determine whether MMFS treatment reduced depression in those who had depression at baseline, we evaluated baseline Geriatric Depression Scale (GDS) score versus the change in GDS score following treatment. There was a significant negative correlation between baseline GDS score and change of GDS at 2 months (R=−0.695, p=0.006), as shown in FIG. 5B. Subjects with higher depression at baseline had greater reduction in depression following magnesium L-threonate treatment. Not wishing to be bound by theory, this trend may indicate that magnesium and/or magnesium L-threonate administration may have a therapeutic effect on depression. Similarly, not all subjects had sleep disorder at baseline, but like depression, there was a significant correlation between baseline sleep score and change in sleep score (Pittsburgh Sleep Quality Index; PSQI) following MgT treatment (R=−0.741, p=0.002), as shown in FIG. 5C. Not wishing to be bound by theory, magnesium and/or magnesium L-threonate administration may be used to treat sleep disorder and/or improve quality of sleep. Not wishing to be bound by theory, magnesium administration may increase a subject's MMSE score or reduce the rate of the decrease of the subject's MMSE score over time. Not wishing to be found by theory, magnesium administration may increase cerebral metabolism and improve the cognitive functioning of the subject.

The present invention also provides kits that can be used to practice the present invention. In an aspect, the present invention provides a kit for administering magnesium threonate to a subject in need of supplementing magnesium. In the kit, at least a portion of magnesium (Mg) and threonate (T) of the magnesium threonate may be present in a salt form of $MgT_2$. The kit may comprise (a) two of a first oral dosage form comprising the magnesium threonate; (b) one of a second oral dosage form comprising the magnesium threonate; and (c) a set of instructions for instructing the subject on (i) consuming the first oral dosage form in daytime, and (ii) consuming a combination of the first and second oral dosage forms at once in nighttime. The first and second oral dosage forms may exhibit different in vitro dissolution profiles in the same dissolution medium. The kit may be formulated such that the kit provides a sufficient amount of the first and second oral dosage forms to be utilized by the subject for at least one month. The kit may be formulated such that the kit provides a sufficient amount of the first and second oral dosage forms to be utilized by the subject for at least 1 month, 2 months, 3 months or longer.

In some embodiments, oral dosage forms comprise of tablets. Tablets are made by methods known in the art and may further comprise suitable binders, fillers, lubricants, diluents, disintegrating agents (dissolution aids), colorants, flavoring agents, flow-inducing agents, melting agents, many varieties of which are known in the art. The oral dosage forms of the present invention may, optionally, have a film coating to protect the components of the magnesium-counter ion supplement composition from one or more of moisture, oxygen and light or to mask any undesirable taste or appearance. Suitable coating agents include, for example, cellulose, hydroxypropylmethyl cellulose, croscarmellose, and ethylcellulose. In some embodiments, the oral dosage form comprises a plurality of beads encapsulated in a capsule. Such format can be used as a controlled release formulation. Other forms of tablets can also be formulated in controlled release format. Methods of making controlled release tablets are known in the art, e.g., see U.S. Patent Publications 2006/051416 and 2007/0065512, or other references disclosed herein.

In some embodiments, oral dosage form according to the present invention are made by mixing a powder comprising magnesium (Mg) and threonate (T), both of which can be present in a salt form, with a polymer in an amount sufficient to create particles comprising the magnesium (Mg), the threonate (T), and the polymer, wherein said particles are of a size sufficient to be retained by a 12 mesh sieve. In some embodiments, the method further comprising: filtering said particles to remove unbound threonate using the 12 mesh sieve; drying the particles; adding an acceptable amount of lubricant to said particles; compressing the particles into one or more pills of total size between about 100 mg and about 2000 mg and coating said one or more pills with a polymer coating comprising one or more of polyvinylpyrrolidone, polyvinyl acetate, and propylene glycol. In some embodiments, the pills are made with an elemental magnesium content of from about 10 mg to about 200 mg. In some embodiments, one or more forms of threonate contained within the dosage form comprises a threonate salt of a threonate precursor molecule as described herein. For example, a precursor may comprise threonic acid, a threonate ester, or a threonate lactone.

In some embodiments, the compositions described herein are prepared using formulations as described in U.S. Pat. No. 4,606,909, entitled "Pharmaceutical multiple-units formulation." This reference describes a controlled release, multiple unit formulation in which a multiplicity of individually coated or microencapsulated units are made available upon disintegration of the formulation (e.g., pill or tablet) in the stomach of the subject (see, for example, column 3, line 26 through column 5, line 10 and column 6, line 29 through column 9, line 16). Each of these individually coated or microencapsulated units contains cross-sectionally substantially homogenous cores containing particles of a sparingly soluble active substance, the cores being coated with a coating that is substantially resistant to gastric conditions but which is erodable under the conditions prevailing in the gastrointestinal tract.

In some embodiments, the composition of the invention are formulated using the methods disclosed in U.S. Pat. No. 4,769,027, entitled "Delivery system," for example. Accordingly, controlled release formulations of physiologically acceptable material (e.g., sugar/starch, salts, and waxes) may be coated with a water permeable polymeric matrix containing magnesium and next overcoated with a water-permeable film containing dispersed within it a water soluble particulate pore forming material.

In some embodiments, the magnesium composition is prepared as described in U.S. Pat. No. 4,897,268, entitled "Drug delivery system and method of making the same," for example, involving a biocompatible, biodegradable microcapsule delivery system. Thus, the magnesium may be formulated as a composition containing a blend of free-flowing spherical particles obtained by individually microencapsulating quantities of magnesium, for example, in different copolymer excipients which biodegrade at different rates, therefore releasing magnesium into the circulation at a predetermined rates. A quantity of these particles may be of such a copolymer excipient that the core active ingredient is released quickly after administration, and thereby delivers the active ingredient for an initial period. A second quantity of the particles is of such type excipient that delivery of the encapsulated ingredient begins as the first quantity's delivery begins to decline. A third quantity of ingredient may be encapsulated with a still different excipient which results in delivery beginning as the delivery of the second quantity beings to decline. The rate of delivery may be altered, for example, by varying the lactide/glycolide ratio in a poly(D, L-lactide-co-glycolide) encapsulation. Other polymers that may be used include polyacetal polymers, polyorthoesters, polyesteramides, polycaprolactone and copolymers thereof, polycarbonates, polyhydroxybuterate and copolymers thereof, polymaleamides, copolyaxalates and polysaccharides.

In some embodiments, the composition of the present invention are prepared as described in U.S. Pat. No. 5,395,626, which features a multilayered controlled release dosage form. The dosage form contains a plurality of coated particles wherein each has multiple layers about a core containing magnesium whereby the magnesium containing core and at least one other layer containing an active ingredient is overcoated with a controlled release barrier layer therefore providing at least two controlled releasing layers of a water soluble composition from the multilayered coated particle.

In some embodiments, the magnesium and threonate is prepared using the OROS® technology, described for example, in U.S. Pat. No. 6,919,373 entitled "Methods and devices for providing prolonged drug therapy;" U.S. Pat. No. 6,923,800, entitled "Osmotic delivery system, osmotic delivery system semipermeable body assembly, and method for controlling delivery rate of beneficial agents from osmotic delivery systems;" U.S. Pat. No. 6,929,803 entitled "Conversion of liquid filled gelatin capsules into controlled release systems by multiple coatings;" and U.S. Pat. No. 6,939,556 entitled "Minimally compliant, volume efficient piston for osmotic drug delivery systems;" all of which are hereby incorporated by reference. This technology employs osmosis to provide precise, controlled delivery for up to 24 hours and can be used with a range of compounds, including those that are poorly soluble. OROS® technology can be used to deliver high doses meeting high loading requirements. By targeting specific areas of the gastrointestinal tract, OROS® technology may provide more efficient absorption and enhanced bioavailability of the active ingredient. The osmotic driving force of OROS® and protection of the active ingredient until the time of release eliminate the variability of absorption and metabolism sometimes caused by gastric pH and motility.

Formulations for continuous long-term delivery are further provided in, e.g., U.S. Pat. No. 6,797,283, entitled "Gastric retention dosage form having multiple layers;" U.S. Pat. No. 6,764,697, entitled "System for delaying drug delivery up to seven hours;" and U.S. Pat. No. 6,635,268, entitled "Sustained delivery of an active agent using an implantable system;" all of which are incorporated herein by reference.

In some embodiments, the controlled release dosage forms of the present invention comprise a plurality of beads, wherein each bead includes a core having a diameter from about 1 micrometer ($\mu$m) to about 1000 $\mu$m and the core includes an active ingredient comprising magnesium or a salt thereof in the range of about 15 to about 350 milligram (mg) of magnesium (Mg)/gram (g) of the dosage form, wherein the dosage forms include less than about 2.5% adduct and has a dissolution rate of the active ingredient of more than about 80% within about the first 60 minutes following entry of the dosage forms into a use environment. In some embodiments, the dissolution rate is more than about 80% within 30 minutes.

In some embodiments, each bead includes a core and an active ingredient comprising magnesium. A suitable bead form of magnesium may comprise magnesium and threonate admixed with soluble components, e.g., sugars (e.g., sucrose, mannitol, etc.), polymers (e.g., polyethylene glycol, hydroxypropyl cellulose, hydroxypropyl methyl cellulose, etc.), surfactants (sodium lauryl sulphate, chremophor, tweens, spans, pluronics, and the like), insoluble glidant components (microcrystalline cellulose, calcium phosphate, talc, fumed silica, and the like), coating material (examples of suitable coating materials are polyethylene glycol, hydroxypropyl methyl cellulose, wax, fatty acids, etc.), dispersions in suitable material (examples are wax, polymers, physiologically acceptable oils, soluble agents, etc.) or combinations of the above.

According to some embodiments, the core includes sugar spheres (nonpareil seeds), microcrystalline cellulose, or mannitol. In some embodiments, the core is a sugar sphere, USP (Paulaur Cranbury, N.J.). In some embodiments, the particle size of the core ranges from about 1 $\mu$m to about 1000 $\mu$m. In some embodiments, the particle size of the core ranges from about 300 $\mu$m to about 900 $\mu$m. In some embodiments, the particle size of the core ranges from about 450 $\mu$m to about 825 $\mu$m. In exemplary embodiments, the core may be coated to avoid interaction between the core and the active ingredient. For example, suitable coating materials include, but are not limited to, polyethylene glycol, hydroxypropyl methyl cellulose, wax, fatty acids, etc.

In one embodiment, the spheres comprise a portion of the dosage form ranging from about 50 mg/g to about 500 mg/g, preferably from about 60 mg elemental magnesium per g of oral dosage form (i.e., 60 mg Mg/g), to about 100 mg elemental magnesium per g of oral dosage form (i.e., 100 mg Mg/g). The fraction of the bead will depend on the amount of additional constituents, if any, used in the dosage form.

The core can be coated with magnesium, e.g., magnesium threonate. In one embodiment, magnesium threonate is present in amounts from about 150 mg/g (or 12.4 mg Mg/g) to about 950 mg/g (or 78.4 mg Mg/g), preferably from about 500 to 900 mg/g (or 41.2 to 74.3 mg Mg/g) based on the weight of the entire immediate release bead. In other embodiments, magnesium is present in amounts from about 15 to 300 mg/g, preferably from about 25 to about 250 mg/g.

In one embodiment, magnesium threonate is added to a mixture of a binder and a glidant prior to coating the core. The glidant may be selected from, but is not limited to, microcrystalline cellulose, calcium phosphate, talc, and fumed silica. Glidants may be used in amounts ranging from 1.5 mg/g to about 35 mg/g. In some embodiments, glidants range from about 1.5 mg/g to about 30 mg/g. In some embodiments, glidants range from about 2.5 mg/g to about 25 mg/g. In another embodiment, the range of glidant is from about 5 mg/g to about 30 mg/g.

The binder may be selected from, but is not limited to, povidone (PVP), croscarmellose, ethylcellulose, hydroxypropyl methylcellulose (HPMC, Opadry), hydroxypropyl cellulose (HPC), or combinations thereof. In an embodiment where the binder is HPMC, the binder is present in an amount ranging from about 15 mg/g to about 30 mg/g, preferably from about 15 mg/g to about 25 mg/g. In another embodiment, where the binder is povidone, the binder is present in an amount of from about 1.5 mg/g to about 35 mg/g, preferably from about 5 mg/g to about 30 mg/g.

The mixture of active ingredient and binder/water/glidant may be prepared by mixing, e.g., with a stirrer, for at least 15 minutes, for at least 30 minutes, or for at least one hour. The components may also be combined by methods including blending, mixing, dissolution and evaporation, or by using suspensions.

The active ingredient/binder/inactives mixture may be deposited on a core, wet massed and extruded, granulated, or spray dried. In one embodiment, sugar spheres are prewarmed to a temperature ranging from about 40° C. to about 55° C. prior to application of the mixture. The core may be optionally coated with from about 2% weight/weight (w/w) to about 10% w/w seal coating prior to applying the active layer. The seal coating may be any applicable coating which can separate any active ingredients from the core, for example, polymer coatings such as Eudragit®, HPMC, HPC, or combinations thereof. For this reason also, dissolution stability (i.e., maintenance of dissolution profile after exposure to elevated temperatures) is important for the compositions of the present invention.

In one embodiment, the sugar sphere are coated with a fluidized bed coater known in the art, for example, a Glatt Powder Coater and Granulator, GPCG3 (Ramsey, N.Y.). One skilled in coating conditions such as air velocity, spray rate, and atomization pressure are typically controlled as is appreciated by and known to those skilled in the art. The temperature range of the product may range from about 43° C. to about 51° C. The air velocity may range from about 5 to about 9 meter per second (m/s). The spray rate ranges from about 9 to about 42 gram per minute (g/min). The atomization pressure can range from about 1.5 to about 2.0 bar. The beads are then dried in the fluidized bed of the coating apparatus at a temperature of about 45° C. to about 50° C. for at least 5 minutes. In some embodiments, the beads are dried for at least 15 minutes, or for at least 30 minutes. One skilled in the art will recognize that many alternate operating conditions and various types of equipment can also be used.

Once the beads are formed as cores containing magnesium threonate as provided herein, the beads may be optionally additionally coated with a seal coating. The seal coating may be a polymer or a combination of polymers that can be designed to be pH dependent or independent. In a preferred embodiment, the polymer for the seal coating is selected from, but not limited to HPMC (Opadry®, Colorcon, Pa.), HPC, Eudragit® RL, Eudragit® E100, Eudragit® E 12.5, Eudragit®, E PO, Eudragit® NE (e.g., NE 30D or NE 40D) and combinations of two or more of the foregoing. These polymers are insoluble in aqueous media but display pH-independent swelling on contact with aqueous fluids. In another embodiment, the beads are coated with pH-dependent polymers, soluble at a pH preferably above 5. In the immediate release bead formulations, the seal coating polymer is present in amounts ranging from about 0% w/w to about 40% w/w, preferably from about 0% w/w to about 10% w/w, more preferably from about 0% w/w to about 3% w/w.

Alternatively the cores may be coated with a rapidly disintegrating or dissolving coat for aesthetic, handling, or stability purposes. Suitable materials are polyvinylpyrrolidone, hydroxypropyl cellulose, hydroxypropyl methyl cellulose, polyethylene glycol, polymethacrylates containing free amino groups, each may be with or without plasticizers, and with or without an antitack agent or filler. An addition of about 3% of the weight of the core as coating material is generally regarded as providing a continuous coat for this size range. The over coating may be a polymer selected from, but are not limited to HPMC (Opadry®, Colorcon, Pa.), HPC, Eudragit® RL, Eudragit® E100, Eudragit® E 12.5, Eudragit® E PO, Eudragit® NE and mixtures thereof.

The beads or bead mixtures may be used, for example, in suspensions, filled into capsules, compressed into tablets, or filled into sachets. One or more types of controlled release beads can be mixed together and encapsulated, or used as a sprinkle on the subject's food. According to the invention, the oral solid dosage form may be any of these forms. Preferably, the dosage form is a capsule. In one embodiment of the invention, the beads are formulated into capsules with the use of an encapsulation machine. Various capsule sizes may be required to accommodate the strength and fill weight of the target formulations. Capsule size range from 00 to 5 for fill weights ranging from about 15 mg to about 630 mg.

The particle sizes of the immediate release and controlled release bead components in the dosage form depend on the technology used to prepare them. The particle sizes component range from submicron to 500 µm for powder technologies (mixtures, spray drying, dispersions etc), 5 to 1700 µm for coating technologies (Wurster®, top spray, bottom spray, spray drying, extrusion, layering, etc.), to 1-40 millimeter (mm) for tabletting technologies.

In addition to the active ingredients comprising magnesium and threonate, the oral dosage forms of the present invention can comprise any numbers of physiologically acceptable excipients, depending in part on the controlled release mechanism to be used. "Physiologically Acceptable" includes molecular entities and compositions that do not produce an adverse, allergic or other untoward reaction when administered to an animal, or a human, as appropriate, e.g., those that are pharmaceutically acceptable. "Physiologically Acceptable Carrier" includes micelles, liposomes, microspheres, nanofibers, and any combination thereof. The physiologically acceptable carrier includes any and all solvents, dispersion media, coatings, antibacterial and antifungal agents, isotonic and absorption delaying agents and the like. The use of such media and agents for physiologically active substances is well known in the art. Except insofar as any conventional media or agent is incompatible with the active ingredient, its use in the magnesium threonate compositions is contemplated. Supplementary active ingredients can also be incorporated into the compositions. "Physiologically Acceptable Salts" include acid addition salts and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. General techniques for formulation and administration are found in "Remington: The Science and Practice of Pharmacy, Twentieth Edition," Lippincott Williams & Wilkins, Philadelphia, Pa. Tablets, capsules, pills, powders, granules, dragees, gels, slurries, ointments, solutions suppositories, injections, inhalants and aerosols are examples of such formulations.

By way of example, controlled release oral formulation can be prepared using additional methods known in the art. For example, a suitable controlled release form of the magnesium threonate compositions provided herein may be a matrix tablet or capsule composition. Suitable matrix forming materials include, for example, waxes (e.g., carnauba wax, bees wax, paraffin wax, ceresine, shellac wax, fatty acids, and fatty alcohols), oils (e.g., hydrogenated vegetable oil), hardened oils or fats (e.g., hardened rapeseed oil, castor oil, beef tallow, palm oil, and soya bean oil), and polymers (e.g., hydroxypropyl cellulose, polyvinylpyrrolidone, hydroxypropyl methyl cellulose, and polyethylene glycol). Other suitable matrix tabletting materials are microcrystalline cellulose, powdered cellulose, hydroxypropyl cellulose, ethyl cellulose, with other carriers, and fillers. Tablets may also contain granulates, coated powders, or pellets. Tablets may also be multi-layered. Multi-layered tablets are useful when the active ingredients, e.g., different forms of magnesium and threonate, have markedly different pharmacokinetic profiles. Optionally, the finished tablet may be coated or uncoated.

The coating composition typically contains an insoluble matrix polymer (approximately 15-85% by weight of the coating composition) and a water soluble material (e.g., approximately 15-85% by weight of the coating composition). Optionally an enteric polymer (approximately 1 to 99% by weight of the coating composition) may be used or included. Suitable water soluble materials include polymers such as polyethylene glycol, hydroxypropyl cellulose, hydroxypropyl methyl cellulose, polyvinylpyrrolidone, polyvinyl alcohol, and monomeric materials such as sugars (e.g., lactose, sucrose, fructose, mannitol and the like), salts (e.g., sodium chloride, potassium chloride and the like), organic acids (e.g., fumaric acid, succinic acid, lactic acid, and tartaric acid), and mixtures thereof. Suitable enteric polymers include hydroxypropyl methyl cellulose, acetate succinate, hydroxypropyl methyl cellulose, phthalate, polyvinyl acetate phthalate, cellulose acetate phthalate, cellulose acetate trimellitate, shellac, zein, and polymethacrylates containing carboxyl groups.

The coating composition may be plasticised according to the properties of the coating blend such as the glass transition temperature of the main component or mixture of components or the solvent used for applying the coating compositions. Suitable plasticisers may be added from 0 to 50% by weight of the coating composition and include, for example, diethyl phthalate, citrate esters, polyethylene glycol, glycerol, acetylated glycerides, acetylated citrate esters, dibutylsebacate, and castor oil. If desired, the coating composition may include a filler. The amount of the filler may be 1% to approximately 99% by weight based on the total weight of the coating composition and may be an insoluble material such as silicon dioxide, titanium dioxide, talc, kaolin, alumina, starch, powdered cellulose, magnesium-comprising component, or polacrilin potassium.

The coating composition may be applied as a solution or latex in organic solvents or aqueous solvents or mixtures thereof. If solutions are applied, the solvent may be present in amounts from approximate by 25-99% by weight based on the total weight of dissolved solids. Suitable solvents are water, lower alcohol, lower chlorinated hydrocarbons, ketones, or mixtures thereof. If latexes are applied, the solvent is present in amounts from approximately 25-97% by weight based on the quantity of polymeric material in the latex. The solvent may be predominantly water.

The compositions of the present invention comprise one or any combinations of excipients such as, but not limited to, diluents, binders, disintegrants, glidants, lubricants, colorants, flavouring agents, solvents, film forming polymers, plasticizers, opacifiers, antiadhesives, and polishing agents. The compositions of the present invention may be formulated using any of the following excipients or combinations thereof.

TABLE 1

Example excipients

| Excipient name | Chemical name | Exemplary Function |
| --- | --- | --- |
| Avicel PH102 | Microcrystalline Cellulose | Filler, binder, wicking, disintegrant |
| Avicel PH101 | Microcrystalline Cellulose | Filler, binder, disintegrant |
| Eudragit RS-30D | Polymethacrylate Poly(ethyl acrylate, nethyl methacrylate, timethylammonioethyl methacrylate chloride) 1:2:0.1 | Film former, tablet binder, tablet diluent; Rate controlling polymer for controlled release |
| Methocel K100M Premium CR | Hydroxypropyl methylcellulose | Rate controlling polymer for controlled release; binder; viscosity-increasing agent |
| Methocel K100M | Hydroxypropyl methylcellulose | Rate controlling polymer for controlled release; binder; viscosity-increasing agent |
| Magnesium Stearate | Magnesium Stearate | Lubricant |
| Talc | Talc | Dissolution control; anti-adherent, glidant |
| Triethyl Citrate | Triethyl Citrate | Plasticizer |
| Methocel E5 | Hydroxypropyl methylcellulose | Film-former |
| Opadry® | Hydroxypropyl methylcellulose | One-step customized coating system which combines polymer, plasticizer and, if desired, pigment in a dry concentrate. |
| Surelease® | Aqueous Ethylcellulose Dispersion | Film-forming polymer; plasticizer and stabilizers. Rate controlling polymer coating. |

The magnesium compositions described herein may also include a carrier such as a solvent, dispersion media, coatings, antibacterial and antifungal agents, isotonic and absorption delaying agents. The use of such media and agents for pharmaceutically active substances is well known in the art. Acceptable salts can also be used in the composition, for example, mineral salts such as hydrochlorides, hydrobromides, phosphates, or sulfates, as well as the salts of organic acids such as acetates, proprionates, malonates, or benzoates. The composition may also contain liquids, such as water, saline, glycerol, and ethanol, as well as substances such as wetting agents, emulsifying agents, or pH buffering agents. Liposomes, such as those described in U.S. Pat. No. 5,422,120, entitled "Heterovesicular liposomes," PCT applications WO 95/13796, entitled "Vesicles with Controlled Release of Actives," or WO 91/14445, entitled "Heterovesicular Liposomes," or European patent EP 524,968 B1, may also be used as a carrier.

The oral dosage forms of the present invention can comprise a variety of excipients. Surfactants which may be used in the present invention as a compressibility augmenting agent generally include all physiologically acceptable, e.g., pharmaceutically-acceptable, surfactants. Suitable anionic surfactants include, for example, those containing carboxylate, sulfonate, and sulfate ions. Those containing carboxylate ions are sometimes referred to as soaps and are generally prepared by saponification of natural fatty acid glycerides in alkaline solutions. The most common cations associated with these surfactants are sodium, potassium, ammonium and triethanolamine. The chain length of the fatty acids range from 12 to 18. Although a large number of alkyl sulfates are available as surfactants, one particularly preferred surfactant is sodium lauryl sulfate, which has an HLB value of about 40.

In the formulation arts, sodium lauryl sulfate has been used as an emulsifying agent in amounts of up to about 0.1% by weight of the formulation. Sodium lauryl sulfate is a water-soluble salt, produced as a white or cream powder, crystals, or flakes and is used as a wetting agent and detergent. Also known as dodecyl sodium sulfate, sodium lauryl sulfate is actually a mixture of sodium alkyl sulfates consisting chiefly of sodium lauryl sulfate. Sodium lauryl sulfate is also known as sulfuric acid monododecyl ester sodium salt. Furthermore, sodium lauryl sulfate is readily available from commercial sources such as Sigma or Aldrich in both solid form and as a solution. The solubility of sodium lauryl sulfate is about 1 gm per 10 millileter (ml)/water. The fatty acids of coconut oil, consisting chiefly of lauric acid, are catalytically hydrogenated to form the corresponding alcohols. The alcohols are then esterified with sulfuric acid (sulfated) and the resulting mixture of alkyl bisulfates (alkyl sulfuric acids) is converted into sodium salts by reacting with alkali under controlled conditions of pH.

Alternative anionic surfactants include docusate salts such as the sodium salt thereof. Other suitable anionic surfactants include, without limitation, alkyl carboxylates, acyl lactylates, alkyl ether carboxylates, N-acyl sarcosinates, polyvalent alkyl carbonates, N-acyl glutamates, fatty acid, polypeptide condensates and sulfuric acid esters.

In other aspects of the invention amphoteric (amphipathic/amphiphilic surfactants), non-ionic surfactants and/or cationic surfactants are included in the coprocessed compositions of the invention. Suitable non-ionic surfactants such as, for example, polyoxyethylene compounds, lecithin, ethoxylated alcohols, ethoxylated esters, ethoxylated amides, polyoxypropylene compounds, propoxylated alcohols, ethoxylated/propoxylated block polymers, propoxylated esters, alkanolamides, amine oxides, fatty acid esters of polyhydric alcohols, ethylene glycol esters, diethylene glycol esters, propylene glycol esters, glycerol esters, polyglycerol fatty acid esters, SPAN's (e.g., sorbitan esters), TWEEN's (i.e., sucrose esters), glucose (dextrose) esters and simethicone.

Other suitable surfactants include acacia, benzalkonium chloride, cholesterol, emulsifying wax, glycerol monostearate, lanolin alcohols, lecithin, poloxamer, polyoxyethylene, and castor oil derivatives. Those skilled in the art will further appreciate that the name and/or method of preparation of the surfactant utilized in the present invention is not determinative of the usefulness of the product.

Highly polar molecules may also be utilized as the compressibility augmenting agent. Such highly polar molecules include certain dyes, particular those which may be capable of binding to the cellulose surface while thereafter creating a relatively hydrophobic environment due to the presence of a hydrophobic portion of the molecule (e.g., a hydrophobic tail) which "points away" from the cellulose surface and discourages hydrophilic surface-to-surface cellulose interactions, such as hydrogen-bonding. Preferably, the dye is one which is physiologically (e.g., pharmaceutically) acceptable for inclusion in solid dosage forms.

Examples of suitable dyes include Congo Red (chemical name: 3,3'-[[1,1'Biphenyl]-4,4'-diylbis-(azo)]bis[4-amino-1-naphthalenesulfonic acid]disodium salt; FD&C Red No. 40 (also known as "Allura Red") (chemical name: Disodium salt of 6-hydroxy-5[(2-methyl-4-sulfophenyl)azo]-2-naphthalenesulfonic acid); FD&C Yellow No. 5 (common name: tartrazine) (chemical name: 5-oxo-1-(p-sulfophenyl)-4-[(p-sulfophenyl)azo]-2-pyrazoline-3-carboxylic acid, trisodium salt); FD&C Yellow No. 6 (common name: Sunset Yellow FCF) (chemical name: Disodium salt of 1-p-sulphophenylazo-2-naphthol-6-sulfonic acid); Ponceau 4R (chemical name: Trisodium-2-hydroxy-1-(4-sulfonato-1-naphthylazo) naphthalene-6,8-disulfonate); Brown HT (chemical name: Disodium 4,4'-(2,4-dihydroxy-5-hydroxymethyl-3,3-phenylene bisazo)di(napthalene-1-sulfonate)); Brilliant Black BN (Chemical name: Tetrasodium 4-acetamido-5-hydroxy-6-[7-sulfonato-4-(4-sulfonatophenylazo)-1-naphthylazo] naphthalene-1,7-disulfonate); Carmoisine (chemical name: Disodium 4-hydroxy-3-(4-sulfanato-1-naphythylazo)Naphthalene-1-sulfonate); Amaranth (chemical name: Trisodium 2-hydroxy-1-(4-sulfonato-1-naphthylazo) naphthalene-3,6-disulfonate); and mixtures thereof.

Other highly polar molecules which may be utilized as the compressibility augmenting agent include optional additional active agents themselves. For example, it is well-known to those skilled in the art that certain classes of pharmaceuticals, such as anti-psychotic drugs, are highly polar in nature and may be utilized as a compressibility augmenting agent in accordance with this invention.

The usable concentration range for the selected surfactant depends in part upon not only its molecular weight but also its degree of foaming, particularly when present in agitated slurries which will be spray dried to form the desired particulate. Thus, in those aspects of the invention where surfactants other than sodium lauryl sulfate are coprocessed with the magnesium threonate, it is to be understood that the surfactant will be present in an amount which enhances the compressibility of the magnesium threonate and yet does not have a degree of foaming which would substantially inhibit spray drying.

In an embodiment utilizing a spray-drying process, an aqueous dispersion of magnesium threonate and a compressibility augmenting agent (for example, a surfactant or silicon dioxide) is brought together with a sufficient volume of hot air to produce evaporation and drying of the liquid droplets. The highly dispersed slurry is pumpable and capable of being atomized. It is sprayed into a current of warm filtered air, which supplies the heat for evaporation and conveys a dried product to a collecting device. The air is then exhausted with the removed moisture. The resultant spray-dried powder particles may be approximately spherical in shape and may be relatively uniform in size, thereby possessing excellent flowability. The coprocessed particles are not necessarily uniform or homogeneous. Other drying techniques such as flash drying, ring drying, micron drying, tray drying, vacuum drying, radio-frequency drying, and possibly microwave drying, may also be used.

Alternatively, all or part of the excipient may be subjected to a wet granulation with an active ingredient. A representative wet granulation includes loading the novel excipient particles into a suitable granulator, such as those available from Baker-Perkins, and granulating the particles together with the active ingredient, preferably using an aqueous granulating liquid. In some embodiments, a portion of the total amount of the novel excipient is wet granulated with the active ingredient, and thereafter the additional portion of the novel excipient is added to the granulate. In yet other embodiments, the additional portion of the novel excipient to be added to the excipient/active ingredient granulate may be substituted with other excipients commonly used by those skilled in the art, depending of course upon the requirements of the particular formulation.

In other embodiments of the invention, a further material is added to the magnesium threonate as a compressibility augmenting agent. Such additional materials include silicon dioxides, non-silicon metal oxides, starches, starch derivatives, surfactants, polyalkylene oxides, cellulose A ethers, celluloses esters, mixtures thereof, and the like. Specific further materials which may be included in the aqueous slurry (and consequently in the resultant agglomerated microcrystalline cellulose excipient) are aluminum oxide, stearic acid, kaolin, polydimethylsiloxane, silica gel, titanium dioxide, diatomaceous earth, pregelatinized starch, corn starch, high amylose corn starch, high amylopectin corn starch, sodium starch glycolate, hydroxylated starch, modified potato starch, mixtures thereof, and the like. These additives may be included in desired amounts which will be apparent to those skilled in the art.

In addition to one or more active ingredients, additional additives known to those skilled in the art can be added to the novel excipient prior to preparation of the final product. For example, if desired, any generally accepted soluble or insoluble inert filler (diluent) material can be included in the final product (e.g., a solid dosage form). Such inert fillers may comprise a monosaccharide, a disaccharide, a polyhydric alcohol, inorganic phosphates, sulfates or carbonates, and/or mixtures thereof. Examples of suitable inert fillers include sucrose, dextrose, lactose, xylitol, fructose, sorbitol, calcium phosphate, calcium sulfate, calcium carbonate, microcrystalline cellulose, mixtures thereof, and the like.

An effective amount of any generally accepted lubricant, including calcium or magnesium soaps may optionally be added to the excipient at the time the magnesium is added, or in any event prior to compression into a solid dosage form. The lubricant may comprise, for example, calcium stearate or magnesium stearate. In embodiments where a surfactant is included as part or all of the compressibility augmenting agent, an additional inclusion lubricant may not be necessary.

The complete mixture, in an amount sufficient to make a uniform batch of tablets, may then subjected to tableting in a conventional production scale tableting machine at normal compression pressures for that machine, e.g., about 1500-10,000 pounds per square inch (lbs/sq in). The mixture should not be compressed to such a degree that there is subsequent difficulty in its hydration when exposed to gastric fluid.

The composition may comprise an excipient that is a swellable material such as a hydrogel in amounts that can swell and expand. Examples of swellable materials include hydrophilic polymers that are lightly cross-linked, such cross-links being formed by covalent or ionic bond, which interact with water and aqueous biological fluids and swell or expand to some equilibrium state. Swellable materials such as hydrogels exhibit the ability to swell in water and retain a significant fraction of water within its structure, and when cross-linked they will not dissolve in the water. Swellable polymers can swell or expand to a very high degree, exhibiting a 2 to 50 fold volume increase. Specific examples of hydrophilic polymeric materials include poly (hydroxyalkyl methacrylate), poly(N-vinyl-2-pyrrolidone), anionic and cationic hydrogels, polyelectrolyte complexes, poly(vinyl alcohol) having a low acetate residual and cross-linked with glyoxal, formaldehyde, or glutaraldehyde, methyl cellulose cross-linked with dialdehyde, a mixture of cross-linked agar and carboxymethyl cellulose, a water insoluble, water-swellable copolymer produced by forming a dispersion of finely divided copolymer of maleic anhydride with styrene, ethylene, propylene, butylene, or isobutylene cross-linked with from 0.001 to about 0.5 moles of a polyunsaturated cross-linking agent per mole of maleic anhydride in the copolymer, water-swellable polymers of N-vinyllactams, cross-linked polyethylene oxides, and the like. Other examples of swellable materials include hydrogels exhibiting a cross-linking of 0.05 to 60%, hydrophilic hydrogels known as Carbopol.™ acidic carboxy polymer, Cyanamer.™ polyacrylamides, cross-linked water-swellable indene-maleic anhydride polymers, Good-rite.™ polyacrylic acid, polyethyleneoxide, starch graft copolymers, Aqua-Keeps.™ acrylate polymer, diester cross-linked polyglucan, and the like. Methods for testing swellable materials with regards to polymer imbibition pressure and hydrogel-water interface interaction are described in U.S. Pat. No. 4,327,725 issued May 4, 1982, titled "Osmotic device with hydrogel driving member".

The tablets of the present invention may also contain effective amounts of coloring agents, (e.g., titanium dioxide, F.D. & C. and D. & C. dyes; see the Kirk-Othmer Encyclopedia of Chemical Technology, Vol. 5, pp. 857-884, hereby incorporated by reference), stabilizers, binders, odor controlling agents, and preservatives.

In some embodiments, the magnesium (Mg) is complexed with an anion selected from the group consisting of chloride, laminate, lactate, gluconate, citrate, malate, succinate, sulfate, propionate, hydroxide, oxide, orotate, phosphate, borate, salicylate, carbonate, bromide, stearate, an amino acid, butyrate, aspartate, ascorbate, picolinate, pantothenate, nicotinate, benzoate, phytate, caseinate, palmitate, pyruvate, and threonate. In some embodiments, the oral dosage forms comprise a metal ion selected from the group consisting of calcium, potassium, sodium, chromium, iron, selenium, zinc, manganese, molybdenum, vanadium, and lithium. In some embodiments, one or more antioxidants are added to the composition, e.g., resveratrol, ellagic acid, quecertin, lipoic acid or vitamin C.

In addition to the excipients listed above, the oral dosage forms of the present invention contain one or more chemicals or one or more extracts obtained from the nature. Listed below are examples of nutritional ingredients and health ingredients that can be provided according to the present invention.

Examples of nutritional ingredients with which magnesium threonate can be mixed include 5-HTP (5-hydroxytryptophan), 7-keto-DHEA (dehydroepiandrosterone), acetate, acetyl-L-carnitine, AE-941, α-carotene, α-hydroxy acids, α-aminohydrocinnamic acid, α-ketoglutarate, α-galactosidase, α-linolenic acid, α-lipoic acid, α-tocopherol, SHA-10, androstenediol, androstenedione, arginine, aspartic acid (aspartate), ascorbic acid, β-alanine, β-alanyl-L-histidine, β-carotene, β-cryptoxanthin, β-D-fructofuranosidase, betadine, β-glucan, β-glycans, betaine, β-sitosterol, β-tocopherol, BMS-214778, calcium carbonate matrix, calcium phosphate, caprylic acid, canthaxanthin, CDP-choline, chelated calcium, cholecalciferol, choline, chondroitin sulfate, citicoline, citric acid, creatine, cryptoxanthin, cysteine, D-calcium pantothenate, dehydroepiandrosterone, delta-tocopherol, dexpanthenol, dextran-iron, DGL (deglycyrrhiziated licorice), EA (Dehydroepiandrosterone), dibencozide, dichloroacetate, dimethylglycine, dimethylsulfone, disodium disuccinate astaxanthin, D,L-phenylalanine, DMAE (Dimethylaminoethanol), D-mannose, DMSO (dimethyl sulfoxide), docosahexaenoic acid, docusate sodium, eburnamenine-14-carboxylic acid, EDTA (ethylenediamine tetraacetic acid), EFA (essential fatty acid), ellagic acid, eicosapentaenoic acid, ferrous gluconate, ferrous sulfate, 5-hydroxytryptophan, flavonoid, folacin, folate, folic acid, forskolin, fructo-oligosaccharides, GABA (gamma-aminobutyric acid), galanthamine hydrobromide, γ-carotene, γ-linolenic acid, γ-oryzanol, γ-glutamylcysteinylglycine, γ-tocopherol, glucosamine, glucosamine sulfate, glutamine, glutamic acid, glutathione, glycerol, glycerophosphocholine, glycine, histidine, HMB (β-hydroxy-β-methylbutyrate monohydrate), hydroxocobalamin, hydroxycitric acid, hydroxymethylbutyrate, hydroxytryptophan, hyoscine butylbromide (scopolamine), hydroxylysine, hydroxyproline, hypoxanthine riboside, indole-3-carbinol, inosine, inositol hexanicotinate, inositol hexaphosphate, isoascorbic acid, isoflavones, isoleucine, lactic acid, L-arginine, L-ascorbic acid, L-asparagine, L-carnitine, L-Dopa, leucine, L-phenylalanine, L-tryptophan, luzindole, lycopene, lysine, malic acid, mesoglycan, methionine, methylcobalamin, methylguanidine acetic acid, methylsulfonylmethane, monounsaturated fatty acid, N-3 fatty acids, N-acetyl cysteine, N-acetyl D-glucosamine, N-acetyl-5-methoxytryptamine, N-acetylaspartic acid, NADH, niacin, nicotinamide adenine dinucleotide, nordihydroguaiaretic acid (NDGA), octacosanol, octanoic acid, oleuropein, omega-3 fatty acids, omega-6 fatty acids, omega-9 fatty acid, PABA (para-aminobenzoic acid), pangamic acid, pantethine, pantothenic acid, pantothenol, perillyl alcohol, PGG-glucan, phenyl acetate, phosphatidylcholine, phosphatidylserine, phytoestrogen, phytonadione, phytosterols, polyphenols, polysaccharide-K, polyunsaturated fatty acids, polyvinylpyrrolidone-iodine, potassium, potassium aspartate, potassium phosphate, povidone-iodine, pregnenolone, progesterone, provitamin a, pteroylglutamic acid, pyridoxine, pyridoxal-5-phosphate, quercetin, quercetin-3-rhamnoglucoside, quercetin-3-rutinoside, quinine, resveratrol, retinol, riboflavin, riboflavin-5-phosphate, salicin, salicylate, SAM-e (S-adenosylmethionine), sitostanol, sitosterol, sitosterolins, sodium alginate, sodium ascorbate, sodium chloride, sodium ferric gluconate, sodium iodide, sodium phenylacetate, sodium phosphate, sorbic acid, stigmasterol, sulforaphane, synephrine, tannic acid, theanine, theobromine, thiamin, thioctic acid, tocopherols, tocotrienols, triacylglycerol lipase, tricholine citrate (TRI), troxerutin, tryptophan, tyrosine, acetyl-L-tyrosine, ubidecarenone, ubiquinone, urosolic acid, usnic acid, valine, vitamin A, vitamin B1, vitamin B12, vitamin B2, vitamin B3, vitamin B5, vitamin B6, vitamin B9, vitamin Bx, vitamin C, vitamin D, vitamin D2, vitamin D3, vitamin E, vitamin G, vitamin H, vitamin K, vitamin M, vitamin 0, vitamin Q10, xylitol, or zeaxanthin.

Examples of nutritional ingredients which are herbal or natural extracts with which magnesium threonate can be incorporated include aaron's rod (*Verbascum thapsus*), *Abelmoschus moschatus*, *Abrus precatorius*, absinthe, abuta, acacia, *Acacia senegal*, acai, acemannan, acerola, achicoria, *Achillea millefolium*, achiote, ackee, aconite, *Aconitum napellus, Acorns calamus* L., *Actaea racemosa* L., *Actinidia chinensis, Actinidia deliciosa*, adam's needle, adelfa, adrue, aegle marmelos, *Aesculus hippocastanum* L., african wild potato, *Agathosma betulina, Agave americana, Agave sisalana, Agrimonia eupatoria, Agrimonia odorata, Agrimonia procera*, agrimony, *Agropyron repens*, aguacate, alanine, *Albahaca morada, Albaricoque, Albarraz, Alchemilla vulgaris*, alcusa, alder, alfalfa, algarrobo, algin, alizarin, *alkanet tinctoria, allium cepa, allium sativum, allium ursinum*, allspice, *almendra amarga, almendra dulce*, aloe, *aloe barbadensis, aloe ferox, aloe vera*, alpine cranberry, *alpinia galanga, alpinia officinarum, althaea officinalis*, aluminum phosphate, *amanita muscaria*, amaranth, amargo, ambrette (*abelmoschus moschatus*), american aloe, american hellebore, american pawpaw, american pennyroyal, american scullcap, american valerian, american white water lily, american yew, aminobenzoic acid, amla fruit, ammi visnaga, amomum, *Anacardium occidentale, Ananas comosus, Ananas sativus*, anapsos, anchusa, andiroba, *Andrographis paniculata, Anemone acutiloba, Angelica sinensis*, angel's trumpet, *Angostura trifoliata, Anis estrellado*, annatto, *Annona muricata*, annual mugwort, annual wormwood, *Antelaea azadirachta, Anthemis grandiflorum, Anthemis nobilis*, anthozoa, antineoplastones, antineoplastons, AFA (*Aphanizomenon flos-aquae*), *Apis cerana, Apis mellifera, Apium graveolens, apocynum cannabinum*, apple cider vinegar, apricot, *Arachis hypogaea, Arbre fricassee*, arbutin, arcilla, *Arctium lappa, Arctium majus*, arctostaphylos, *Arctostaphylos uva-ursi, Areca catechu* L., arecoline, aristolochia, *Armeniaca vulgaris, Armoracia rusticana, Arnica montana*, arrowroot, *Arsenicum album, Artemisia absinthium, Artemisia annua, Artemisia vulgaris, Arthrospira plantensis*, artichoke, *Artocarpus heterophyllus, Arundinaria japonica*, asafoetida, asarabacca, asarum, *Asclepias tuberosa, Ascophyllum nodosum*, ashwagandha, asian ginseng, *Asimina americana, Asimina triloba, Asophyllum nodosum, Aspalathus linearis*, asparagus, *Asparagus officinalis*, aspen, *Asperula odorata, Aspérula olorosa*, astaxanthin, astaxantina, asthma weed, astrágalo, *Astragalus, Astragalus membranaceus, Atropa belladonna*, australian tea tree oil, autumn crocus, aveloz, avena extract, avocado, *Azadirachta indica*, ba ji tian, babassu, *Baccharis genistelloides, Baccharis trimera, Baccharis triptera, Bacopa, Bacopa monnieri*, bael fruit, baikal skullcap, *Ballota nigra*, balm of gilead, balsam herb, bamboo, bantu tulip, *Banxia houpo tang, Baptisia australis*, barbados cherry, barberry, bardana, *Barosma betulina*, bay leaf, bayberry, bear's garlic, bearberry, bedstraw, bee pollen, beeswax, beet, *Bejunco de cerca*, belcho (*Ephedra sinica*), belladona, *Bellis perennis*, bentonite, *Berberina*, berberine, *Berberis aristata, Berberis vulgaris*, bergamot oil, β-vulgaris, betel nut, betony, *betula* spp., bifidobacteria, bilberry, biminne, bing gan tang, birch sugar, birthwort, bishop's weed, bismuth, bitter almond, bitter aloe, bitter ash, bitter gourd, bitter melon, bitter orange, bitter wood, bitterroot, *Bixa orellana*, biznaga, black bryony, black cohosh, black currant, black haw, black horehound, black mulberry, black mufstard oil, black pepper, black seed, black tea, blackberry, black cherry, black walnut, bladderwrack, blessed thistle, *Blighia sapida*, bloodroot, blue cohosh, blue flag root, blue rocket (aconite), blueberry, blue-green algae, bluperum, boldo, boneset, borage seed oil, *Borago officinalis*, borforsin, *Boswelia carterii, Boswellia sacra, Boswellia serrata*, bovine cartilage, boxwood, brahmi, *Brassica campestris* oil, *Brassica nigra, Brassica oleracea*, brazilian vetiver, bromelain, broom corn, brugmansia, bryonia, b-sitosterol, buchu, buckhorn plantain, buckshorn plantain, buckthorn, buckwheat, bugleweed, bulbous buttercup, bupleurum, burdock, butanediol, butcher's broom, butterbur, *Buxus sempervirens* L., cabbage rose, cactus prickly pear, cajeput oil, calaguala, calamus, calcitriol, calendula, california jimson weed, california poppy, *Calophyllum inophyllum* L., *Calostro bovino, Camellia sinensis*, campesterol, camphor, canadian hemp, cancer weed, *Cannabis sativa*, canola oil, cantharis, *Capsella bursa pastoris*, capsicum, *carapa* ssp., caraway, caraway oil, carbohydrate supplement, cardamom, cardamomo, *Cardo bendito, Cardo lechero, Carica papaya*, carnitine, carnosine, carob, carotene, carqueja (*Baccharis genistelloides*), carrageenan, carrot, *Carthamus tinctorius, Cascara sagrada*, cashew, *Castaña de indias*, castor oil, castor seed, caterpillar fungus, *Catha edulis*, catnip, cat's claw, cat's hair, catuaba, *Caulophyllum thalictroides*, cayenne, cebada, *Cebolla albarrana*, cedar leaf oil, celandine, cemphire, *Centaurea benedicta, Centaurea cyanus, Centella asiatica*, century plant (*Agave americanan*), *Cephaelis ipecacuanha, Ceratonia asiatica, Ceratonia siliqua, Cervus elaphus, Cervus nippon, Cetyl myristoleate, Ceylon citronella, Chamaemelum nobile*, chamomile, chaparral, chasteberry, chaste tree, *Chelidonium majus, Chenopodium quina, Chenopodium vulvaria*, chewing tobacco, chia, chickweed, chicory, chili pepper, china rose, chinese angelica, chinese boxthorn, chinese foxglove, chinese gelatin, chinese ginger, chinese ginseng, chinese matrimony vine, chinese star anise, chinese wormwood, chintul, chirayata, chitosan, *chlorella*, Cholestin®, chrysanthemum, *Chrysanthemum vulgare*, chrysin, *chrysopogon* spp., *Cichorium intybus, Cicuta virosa*, cider vinegar, *Cimicifuga racemosa, Cinnamomum aromaticum*, cinnamon, *Cissampelos pareira, Citrillus colocynthis*, citronella grass, citrulline, *Citrus aurantifolia, Citrus aurantium, Citrus bergamia, Citrus naringinine, Citrus paradisi, Citrus reticulata, Claviceps purpurea, Clavo de olor*, cloud mushroom, clove, club moss, *Cnidium monnieri*, cobalamin, coca, *Coccinia indica, Cochlearia armoracia*, cockleburr, coconut oil, codonopsis, coenzyme Q10, coenzyme R, *Cohosh azul, Cohosh negro*, cola nut, colchicum, *Coleus forskohlii*, coltsfoot, *Colubrina arborescens*, comfrey, *Commifora mukul, Commiphora molmol, Commiphora myrrha*, condurango, cone flower, *Conium maculatum*, consuelda, *Copaiba balsam, Copaifera officinalis*, coptis formula, coral calcium, *Cordyceps sinensis*, Coriolus mushroom, *Coriolus versicolor*, corn poppy, corn silk, corn sugar gum, cornflower, *cornus* spp., corydalis, *Corylus avellana, Corynanthe Yohimbi*, costmary, cottonseed oil, cottonwood, couch grass, cow parsnip, cowbane, cowhage, cowslip (*Primula veris*), crab's eye, cramp bark, cranberry, cranesbill, *Crataegus*, cumin, creosote bush, *Cucurbita pepo, Cupressus sempervirens, Curcuma domestica, Curcuma longa*, curcumin, curly dock, *Cusparia febrifuga, Cusparia trifoliata*, cuspidatum, custard apple, *Cyamopsis tetragonolobus*, cyanocobalamin, *cymbopogon* spp., *Cynara scolymus, Cyperus articulatus*, cypress, *Cypripedium acaule, Cypripedium calceolus*, cystadane, *Cytisus scoparius*, daio-kanzo-to, daisy, damiana, dandelion, dangshen (or danshen), date palm, *Datura meteloides, Datura sauveolens, Datura stramonium, Datura wrightii, Daucus carota*, deadly nightshade, deanol, deer velvet, desert parsley, devil's claw, devil's club, di huang, diente de leon, diet, macrobiotic, dietary fiber, dietary saccharides, digitalis, dill, *Dioscorea communis, Dioscorea villosa* L., diviner's sage, dogwood, *Dolichos pruriens*, dolomite, dong quai, D-pantothenic acid, D-phenylalanine, *Dromaius novaehollandiae*, drosera, dumontiaceae, dutchman's pipe, eastern hemlock, echinacea, *Echinacea angustifolia, Echinacea purpurea*, echium, elderberry, elecampane, electro colloidal silver, elemental iron, *Elettaria cardamomum, Eleusine indica, Elletaria cardamomum, Elymus repens*, emu oil, enebrina, english chamomile, english ivy, english walnut, english yew, ephedra, EGCG (Epigallocatechin gallate), *Epilobium angustifolium, Epilobium parviflorum, Epimedium grandiflorum*, equinácea, *Equisetum arvense* L., ergocalciferol, *Eriodictyon californicum, Erythroxylum vacciniifolium, Eschscholzia californica, Escoba negra*, espirulina, Essiac®, estevia, eucalyptus oil, euforbio, eufrasia, *Eugenia aromatica, Eupatorium perfoliatum*, euphorbia, euphorbiaceae, *Euphrasia officinalis*, european cranberry, *Euterpe oleracea*, evening primrose oil, *Evodia rutecarpa*, eyebright, *Fagopyrum esculentum*, fennel (*Foeniculum vulgare* mill.), fenugreek, fermented milk, *Ferula assafoetida*, feverfew, *fucus carica*, fucus inspida, fig, filipendula ulmaria, fireweed, flaxseed and flaxseed oil, fleet phospho-soda, fleet enema, Flor-Essence®, fly agaric, fo-ti, foxglove, fragaria, *Fragaria vesca*, frambuesa, *Frangula purshiana*, frankincense, fraxinus, french rose, friar's cap, *Fructus barbarum, Fucus vesiculosus, Fuzheng jiedu tang*, gallic acid, galanga, galanthus, *Galipea officinalis, Galium odoratum, Gallium aparine, Gambierdiscus toxicus, Ganoderma lucidum, Garcinia cambogia, Garcinia mangostana*, farcinia, ácido hydroxicitrico, garlic, garra del diablo (*Harpagophytum procumbens*), gelatin, *Gelidiella acerosa*, gelsemium, genistein, gentian, gentian violet, *Geranium maculatum*, german chamomile, germander, germanio, germanium, *Germanium sesquioxide*, germinated barley foodstuffs, giant knotweed, gimnema, gentian, ginger, ginkgo, ginseng, *Glechoma hederacea*, globe artichoke, glycine soja, *Glycyrrhiza glabra*, gobi, goji, goldenrod, goldenseal, *goniopora* spp., goosegrass, gossypol, gotu kola, gotu kola y fracción triterpénica total de lacentella asiatica (TTFCA), you qi (chinese wolfberry), gramilla, granada, grape seed extract, grapefruit, grass pea, graviola, greater celandine, greater galangal, green hellebore, green tea, griffonia, *Grifola frondosa*, grindelia, *Grindelia camporum*, ground ivy, guar gum, guarana, guayule, guelder rose, guggals, guggul, gum acacia, gum arabic, gumweed, guru nut, *Gymnema sylvestre, Gynostemma pentaphyllum*, hamamelis, *Hange koboku-to*, haritaki, *Harpagophytum procumbens*, hashish, hawthorn, hazelnut, *Hedeoma pulegioides* L., *Hedera helix, Helianthus annuus*, hellebore, hemlock, hemp seed oil, hepatica, *Heracleum maximum*, hesperidin, hibiscus, *Hiedra terrestre, Hierba carmin, Hierba de cabra en celo* (*Epimedium grandiflorum*), *Hierba de limon* (lemon grass), *Hierba de san juan* (*Hypericum perforatum* L.), *Hierba de trigo* (*Triticum aestivum*), high bush cranberry, *Hippophae rhamnoides*, holy basil, *Hochuekki-to*, honey, honeysuckle, *Hongo maitake, Hoodia gordonii, Hordeum vulgare*, horehound, horny goat weed, horse chestnut, horse chestnut seed extract, horse heal, horseradish, horsetail, hou po (magnolia bark), hoxsey formula, huang qi, huang-teng ken, *Humulus lupulus* L., *Huperzia serrata*, huperzine A, hyaluronic acid, *Hydrangea arborescens*, *Hydrastis canadensis*, hydrazine sulfate, *Hydrocotyle asiatica*, hydrilla, *Hypericum perforatum*, *Hypoxis hemerocallidea*, *Hypoxis rooperi*, *Hyssopus officinalis*, ignacia (or ignatia), *Illicium verum*, *Impatiens biflora*, *Impatiens pallida*, indian bael, indian barberry, indian fig, indian licorice, indian mulberry, indian poke, indian snakeroot, indian tobacco, *Inula campana*, *Inula helenium*, ipecac, *Ipomoea orizabensis*, ipriflavone, iris versicolor, *Isatis indigotica*, iscador, isphagula, ivy, jackfruit, jamaican quassia, japanese yew, japanese sophora, jasmine, jengibre, jequirity, jervine alkaloids, jewelweed, jianpi wenshen recipe, jiaogulan, jimson weed, jointed flatsedge, jojoba, joshua tree, *Juglans regia*, juniper, kan Jang®, karaya gum, karkada, katuka, kale, kava (*Piper methysticum*), kefir, kelp, khat (*Catha edulis*), khella (*Ammi visnaga*, also known as khellin), kinetin, kiwi, kiwifruit, klamath weed, kola nut, korean red *ginseng*, krebiozen, krestin, krill oil, kudzu, labrador tea, lactalbumin, *Lactobacillus acidophilus*, *Lactobacillus casei*, *Lactobacillus* GG, *Lactobacillus plantarum*, *Lactobacillus reuteri*, *Lactobacillus sporogenes*, *Lactobacilo acidófilo*, lactoferrin, ladies mantle, lady's slipper, laetrile, *Lagerstroemia speciosa* L., larch arabinogalactan, larix, *Larrea divaricata*, *Larrea tridentata*, lathyrus, *Laurus nobilis*, *Laurus persea*, lavender, lecithin, *Ledum groenlandicum*, *Ledum latifolium*, *Ledum palustre*, legume, lei gong teng, lemon balm, lemongrass, lentinan, *Lentinula edodes*, *Lentinus edodes*, lentisco, *Leonurus cardiaca*, *Lepidium meyenii*, *Lepidium peruvianum chacón*, Lesser celandine, lesser galangal, *Lessertia frutescens*, *Levisticum officinale*, levoglutamide, lichen, licorice, lignans, *ligustrum*, lime, lime flower, linden, lingonberry, linseed oil, *Linum usitatissimum*, lipase, lirio azul, lirio de agua blanco (*Nymphaea odorata*), liverwort, L-norvaline, *Lobelia inflata*, locust bean, lomatium, *Lomatium dissectum*, long pepper, *lonicera* spp., *Lophosphora* spp., *Lophosphora williamsii*, lorenzo's oil, lotus, lousewort, lovage, lucky nut, lúpulo, lutein, luteina, *Lycopersicon esculentum*, *Lycopodium clavatum*, *Lycopodium serrata*, *Lycopus americanus*, *Lycopus europaeus*, *Lycopus lucidus*, *Lycopus virginicus*, *Lysichiton americanu*, ma huang, maca (*Lepidium peruvianum* chacon), macrobiotic diet, madagascar jewel, madder (*Rubia tinctorum*), maeng lak kha, magic mint, magnolia, magnolia and pinelliae formula, mahonia, maidenhair tree, maitake mushroom, *Malpidnia glabra*, *Malpighia glabra*, *Malpighia punicifolia*, *malus sylvestris*, *Maltas malvavisco*, mangaresa, mandarin, mangosteen, manto de nuestra señora (*Alchemilla vulgaris*), manzanilla, MAP30, *Maranta arundinacea*, *Maria pastora*, marigold, marijuana, *Marrubio blanco*, *Marrubium vulgare*, marsh tea, marshmallow, marshmallow root, mastic (*Psitacia lentiscus*), *Matricaria recutita*, mauby bark, MCP (modified citrus pectin), meadowsweet, *Medicago sativa* L., *Melaleuca alternifolia*, *Melaleuca leucadendron*, *Melaleuca quinquenervia*, melatonin, *Melissa officinalis*, menaquinones, *Mentha pulegium* L., *Mentha x piperita* L., menthol, mexican scammony root, mezereon, microcrystalline cellulose, microcrystalline hydroxyapatite, milenrama, milk bush, milk thistle, mistletoe, modified citrus pectin, *Momordica charantia* L. curcurbitaceae, *Momordica grosvenori*, monacolin K, *Monascus purpureus*, monkshood, *Moringa citrifolia*, *Moringa officinalis*, moringa, *Morus nigra*, motherwort, mountain balm, moutan, MSM (Methyl sulfonylmethane), *Mucuna pruriens*, mugwort, *Muira puama*, mulberry, mullein, musk seed, mustard, myrcia, *Myrica cerifera*, myrrh, narrowleaf plantain, *Nasturtium officinale*, neem, *Nelumbo nucifera*, neovastat, *Nepeta cataria*, *Nerium oleander*, nettle, nexrutine, *Nicotiana glauca*, *Nicotiana tabacum*, *Nigella sativa*, noni (*Morinda citrifolia*), nopal, northern prickly ash, norvaline, nuez de betel (*Areca catechu* L.), nutmeg, *Nux vomica*, *Nymphaea odorata*, oak bark, oak moss, oat beta-glucan, oat bran/straw, oat, *Ocimum basilicum*, *Ocimum sanctum* L., *Oenothera biennis* L., okra, old man's beard, *Olea europaea*, oleander, olibanum, olive leaf, olive oil, olmo resbaladizo, *Oplopanax horridus*, *Opuntia streptacantha*, *Orbignya phalerata*, oregano, oregon grape, *Origanum vulgare*, ornithine, ovoester, oxerutin, oxykrinin, ox bile extract, pacific yew, pagoda tree, palm oil, palma enana americana (*Serenoa repens*), pamabrom, *Panax ginseng*, *Papaver rhoeas*, *Parietaria officinalis*, parsley, parsnip, *Parthenium argentatum*, parthenolide, pasiflora, passion flower, pastinaca, *Pastinaca sativa*, pau d'arco, *Paullinia cupana*, *Pausinystalia yohimbe*, PC-SPES, peanut oil, pectin, pedicularis, pedra hume caá (*Myrcia salicifolia*), pellitory-of-the-wall, pencil tree, pennyroyal (*Mentha pulegium*), peony, peppermint, peppermint oil, *Perilla frutescens*, periwinkle, *Persea americana*, petadolex, petasita, *Petasites hybridus*, petty spurge, *Peumus boldus*, peyote, phaseolamin (white kidney bean), *Phaseolus vulgaris* varieties, *Phoenix dactylifera*, *Phoradendron leucarpum*, phyllanthus, *Physalis somnifera*, phyto-1, *Phytolacca americana*, *Picraena excelsa*, *Picrasma excelsa*, *Picrorhiza kurroa*, pill-bearing spurge, *Pimenta dioica*, *Pimpinella anisum*, pine bark extract, pine pollen, *Pinus maritima*, *Pinus palustris*, *Piper methysticum*, *Piper nigrum*, *Pistacia lentiscus*, plant stanol ester, *Plantago coronopus*, *Plantago isphagula*, *Plantago lanceolata*, *Plantago ovata*, pleurisy, *Podophyllum hexandrum*, *Podophyllum peltatum*, poinsettia, poison ivy, poke root, pokeweed, poleo americano, policosanol, *Polygonum cuspidatum*, *Polygonum multiflorum*, *Polypodium leucotomos* extract and anapsos, pomegranate, *populus*, poppy, precatory bean, prickly ash, prickly pear cactus, *Primula officinalis*, *Primula veris*, probeta, promensil, propagermanium, propolis, *Prunella vulgaris*, *Prunus africanum*, *Prunus amygdalus*, *Prunus amygdulus dulcis*, *Prunus armeniaca*, *prunus armeniaca* L., psyllium, *Ptychopetalum olacoides*, *Pueraria lobata*, *Pueraria montana* var., puerarin, puerto rican cherry, pulegone, pulsatilla, pumpkin, pumpkin seed oil, *Punica granatum*, purple viper bugloss, pycnogenol, pygeum bark, *Pyrus communis*, pyruvate, qing hao, qinghao, qinghaosu, quack grass, quaker bonnet, quaker buttons, quaking aspen, quassia, queen anne's lace, queen of fruits (*Mangosteen fruts*), queen of the meadow, queen's crape myrtle, *Quercus alba*, *Quercus cortex*, *Quercus marina*, quick-in-the-hand (jewelweed), quimsa-kuchu, quinoa, quinsu-cucho, quitch grass, *Rabdosia rubescens*, radium weed, *Radix angelica sinensis*, *Ranunculus bulbosus*, *Ranunculus ficaria*, rapeseed oil, raspberry, *Rauvolfia serpentine*, red algae, red clover, red palm oil, red sorrel, red stinkwood, red yeast rice, regaliz, rehmannia, *Rehmannia glutinosa*, reina de los prados (*Spiraea ulmaria*), reishi mushroom, rennet, *Rhamnus purshiana*, *Rheum officinale*, *Rheum palmatum*, rhodiola, *Rhodiola rosea*, *Rhododendron tomentosum*, rhubarb, *Rhus tox*, *Ribes nigrum*, rice bran oil, ricola, *Roble blanco*, roman chamomile, romero, rooibos, *Rosa canina*, rosary pea, rose haw, rose hip, rose laurel, roselle, rosemary, *Rosmarinus officinalis* L., royal jelly, rhubarb, *Rubus fructicosus*, *Rubus idaeus*, *Rubus villosus*, ruibarbo, rumalon, *Rumex crispus*, *Ruscus aculeatus*, *Ruta graveolens*, rutin, rye grass, *Sabal serrulata*, sabila, *Saccharomyces cerevisiae*, *Saccharomyces boulardii*, *Saccharomyces thermophilus*, safflower, sage, saiboku-to, saiko-keishi-to, Salba®, *Salix alba, Salix* spp., *Salvia divinorum, Salvia hispanica, Salvia lavandulaefolia, Salvia lavandulifolia, Salvia miltiorrhiza, Salvia officinalis*, samambaia, *Sambucas nigra*, sandalwood, *Sanguinaria canadensis*, sanguinarine, *Santalum album*, sarsaparilla, sassafras, sauco berry (*Sambucus nigra*), saw palmetto, *Schizandra chinensis*, schizandra berry, schizandrae, schizopeta, scopolamine, scotch broom, scullcap, *Scutellaria baicalensis, Scutellaria barbata, Scutellaria lateriflora*, sea buckthorn, seaweed, bladderwrack, *Secale cereale*, secretin, seer sage, sehydrin, sea cucumber, selagine, senna, serine, *Serenoa repens*, sesame oil, seso vegetal, shakuyaku-kanzo-to, shallot, shark cartilage, sheng dihuang, shepherd's purse, shepherd's purse, shiitake mushroom, shikonin, sho seiryu to, sho-saiko-to, shuang huang lian, siamese ginger, silka deer, silver birch, silver protein, silymarin, *Simmondsia chinensis*, sisal, skunk cabbage, slippery elm, *smilax* spp., smokeless tobacco, snakeroot, snowball bush, soja, *Solidago virgaurea*, sophora, *Sorghum vulgare*, sorrel, sour cherry, sour orange juice, soy, soy bean extract, soy bran, soy protein, soy sprouts, soybean oil, sparteine, spinach, spirogermanium, spirulina, spurge olive, squill, st. ignatius bean, st. john's bread, st. john's wort, *Stachys betonica, Stachys officinalis, Star anise, Stellaria media, Sterculia urens*, Stevia, stickleburr, stinging nettle, stinking goosefoot, *Strychnos ignatii, Strychnos nux-vomica, Styphnolobium japonicum*, substance x, sulfato de condroitina, suma (*Pfaffia paniculata*), sunflower seed oil, *Sutherlandia frutescens*, swamp hellebore, sweet almond, sweet annie, sweet basil, sweet cherry, sweet orange, sweet root, sweet woodruff, sweet wormwood, sweetflag, symphytum, *Symphytum officinale, Symplocarpus foetidus*, tadenan, tamanu, tamarind, *Tamarindus indica* L., *Tamus communis, Tanacetum parthenium, Tanacetum vulgare*, tangerine, tansy, *Taraxacum officinale*, taurine, tea tree oil, tejo, terminalia, *Teucrium chamaedrys, Theobroma cacao, Thevetia peruviana, Thuja occidentalis*, thunder god vine, thyme (*Thymus vulgaris*), tibetan goji berry, tilofora, toki-shakuyaku-san, *Toxicodendron radicans* (eastern poison ivy), tragacanth, tree tobacco, trembling aspen, *Tribulus terrestris, Trichilia catigua*, trierucate oil, *Trifolium pratense, Trigonella foenum-graecum, Trigonella foenum-graecum* L. leguminosae, trimethylethanolamine, *Tripterygium wilfordii, Triticum aestivum, Tsuga canadensis*, TTFCA (total triterpenic fraction of *Centella asiatica*), tuftsin, tulsi holy basil, turkey tail mushroom, turmeric, *Turnera aphrodisiaca, Turnera diffusa*, turpentine oil, *Tussilago farfara*, tylophora, *Tylophora indica*, Ukrain™, *Ulmus rubra/Ulmus fulva*, umbrella arum, *Uncaria guianensis, Uncaria tomentosa, Urginea maritima, Urtica dioica, Usnea barbata, Uva ursi, Vaccinium angustifolium, Vaccinium macrocarpon, Vaccinium myrtillus anthocyanoside, Vaccinium vitis-idaea*, valerian, velvet deer antler, velvet flower, velvetleaf, *Veratrum viride, Verbascum thapsus*, verbena, vervain, vetchling, vetiver (*Chrysopogon zizanioides*), *Viburnum opulus, Viburnum prunifolium, Vinagre de sidra de* manzana, *Vinca minor*, vinpocetine, viper's bugloss, virginia's herbal E-Tonic™, *Viscum album* L., *Vitex agnus-castus, Vitis vinifera, Vulvaria, wasabia japonica*, water hemlock, watercress, wheatgrass, wheat bran/grass, wheat germ, wheat sprouts, whey protein, white horehound, white mallow, white oak, white pepper, white sandalwood, white tea, white water lily, wild arrach, wild carrot, wild cherry, wild ginger, wild indigo, wild marjoram, wild rosemary, wild yam, willow bark, witch hazel, *Withania somnifera*, wintergreen, wood betony, wolfberry, wormwood, Xango®, xanthan gum, *Xanthomonas campestris*, xhoba, xi yang shen, xi zhang hu huang Tian, xian cao, xian ling pi, xianxao, xiao qing long tang, xiao-chai-hu-tang, xu ku cao, xue zhi kang, yadake, yagona, yam, yamabushitake mushroom, yang-mei, yangona, yaqona, yarrow, yashti-madhu, yashti-madhuka, yavatikta, yege, yellow astringent, yellow bark, yellow beeswax, yellow beet, yellow broom, yellow dock, yellow ginseng, yellow horse, yellow indian paint, yellow indigo, yellow jasmine, yellow oleander, yellow poppy, yellow puccoon, yellow root, yellow sandalwood, yellow saunders, yellow starwort, *Yemen myrrh, Yerba dulce, Yerba mate, Yerba santa*, yew, yi zhu, yin yang huo, yinhsing, yodo, *Yogaraj guggul* gum resin, yohimbe bark extract (*Pausinystalia yohimbe*), yongona, yuan hu suo, yucca, *Yucca aloifolia, Yucca angustifolia, Yucca arborescens, Yucca breifolia, Yucca filamentosa, Yucca glauca, Yucca schidigera, Yucca whipplei*, yun zhi, *Zanthoxylum americanum, Zapatilla de dama, Zea mays*, Zemaphyte®, *Zingiber officinale* roscoe, or ZMA™. The composition may be used as nutritional supplement, dietary supplement, food supplement, or as a food additive. The composition may be manufactured as a tablet, capsule, liquid, lyophilized powder, powder, crystalline, aerosol, liquid impregnated onto a dermal patch, ointment, or suppository.

In a related embodiment, the magnesium-counter ion composition may also contain other nutritional ingredients including, without limitation, calcium-containing materials such as calcium carbonate, stannol esters, hydroxycitric acid, vitamins, minerals, herbals, spices and mixtures thereof. Examples of vitamins that are available as additional ingredients include, but are not limited to, vitamin A (retinol), vitamin D (cholecalciferol), vitamin E group (alpha-tocopherol and other tocopherols), vitamin K group (phylloquinones and menaquinones), thiamine (vitamin $B_1$), riboflavin (vitamin $B_2$), niacin, vitamin $B_6$ group, folic acid, vitamin $B_{12}$ (cobalamins), biotin, vitamin C (ascorbic acid), and mixtures thereof. The amount of vitamin or vitamins present in the final product is dependent on the particular vitamin. Examples of minerals that are available as additional ingredients include, but are not limited to, calcium, phosphorus, iron, zinc, iodine, selenium, potassium, copper, manganese, molybdenum and mixtures thereof. As is the case with vitamins, the amount of mineral or minerals present in the final product is dependent on the particular mineral. It will be clear to one of skill in the art that the present list of additional neutriceutical components are provided by way of example only, and are not intended to be limiting.

In addition to oral dosage forms, the compositions of the present invention can be administered to a subject by any available and effective delivery systems. Such delivery systems include, but are not limited to, parenteral, transdermal, intranasal, sublingual, transmucosal, intra-arterial, or intradermal modes of administration in dosage unit formulations containing conventional nontoxic physiologically acceptable carriers, adjuvants, and vehicles as desired, such as a depot or a controlled release formulation. Depending on the route of administration, the magnesium composition of the present invention may be formulated as a suppository, lotion, patch, or device (e.g., a subdermally implantable delivery device or an inhalation pump). The compositions may be optimized for particular types of delivery.

In some embodiments of the present invention, magnesium and threonate are delivered in an aerosol spray preparation from a pressurized pack, a nebulizer or from a dry powder inhaler. Suitable propellants that can be used in a nebulizer include, for example, dichlorodifluoro-methane, trichlorofluoromethane, dichlorotetrafluoroethane and carbon dioxide. The dosage can be determined by providing a valve to deliver a regulated amount of the compound in the case of a pressurized aerosol.

Compositions for inhalation or insufflation include solutions and suspensions in pharmaceutically acceptable, aqueous or organic solvents, or mixtures thereof, and powders. The liquid or solid compositions may contain suitable excipients as set out above. Preferably the compositions of the present invention are administered by the oral, intranasal or respiratory route for local or systemic effect. Compositions in acceptable solvents may be nebulized by use of inert gases. Nebulized solutions may be breathed directly from the nebulizing device or the nebulizing device may be attached to a face mask, tent or intermittent positive pressure breathing machine. Solution, suspension or powder compositions may be administered, preferably orally or nasally, from devices that deliver the formulation in an appropriate manner.

In some embodiments, for example, the composition may be delivered intranasally to the cribriform plate rather than by inhalation to enable transfer of the active agents through the olfactory passages into the central nervous system (CNS) and reducing the systemic administration. Devices commonly used for this route of administration are included in U.S. Pat. No. 6,715,485, entitled "Nasal delivery device." Compositions delivered via this route may enable increased CNS dosing or reduced total body burden reducing systemic toxicity risks associated with certain compositions.

The composition may optionally be formulated for delivery in a vessel that provides for continuous long-term delivery, e.g., for delivery up to 30 days, 60 days, 90 days, 180 days, or one year. For example the vessel can be provided in a biocompatible material such as titanium. Long-term delivery formulations are particularly useful in subjects with chronic conditions, for assuring improved patient compliance, and for enhancing the stability of the compositions.

According to another embodiment, the composition of the invention is a liquid or semi liquid comprising at least 20 milligram per liter (mg/L) magnesium, or at least 40 mg/L magnesium. In some embodiments, the composition of the invention is a liquid or semi liquid comprising at least 5 mg/L magnesium, at least 10 mg/L magnesium, at least 20 mg/L magnesium, at least 30 mg/L magnesium, at least 40 mg/L magnesium, at least 50 mg/L magnesium, at least 60 mg/L magnesium, at least 70 mg/L magnesium, at least 80 mg/L magnesium, at least 90 mg/L magnesium, or at least 100 mg/L magnesium.

Alternatively, the compositions of the present invention may be administered transdermally. Preparation for delivery in a transdermal patch can be performed using methods also known in the art, including those described generally in, e.g., U.S. Pat. Nos. 5,186,938 and 6,183,770, 4,861,800, 6,743, 211, 6,945,952, 4,284,444, and WO 89/09051, incorporated herein by reference in their entireties. A patch is a particularly useful embodiment with active agents having absorption problems. Patches can be made to control the release of skin-permeable active ingredients over a 12 hour, 24 hour, 3 day, and 7 day period. In one example, a 2-fold daily excess of magnesium threonate is placed in a non-volatile fluid. A preferred release can be from 12 to 72 hours.

In some embodiments, for example, the composition may be delivered via intranasal, buccal, or sublingual routes to the brain rather than by inhalation to enable transfer of the active agents through the olfactory passages into the CNS and reducing the systemic administration. Devices commonly used for this route of administration are included in U.S. Pat. No. 6,715,485, entitled "Nasal delivery device." Compositions delivered via this route may enable increased CNS dosing or reduced total body burden reducing systemic toxicity risks, e.g., diarrhea.

Preparation of a compositions for delivery in a subdermally implantable device can be performed using methods known in the art, such as those described in, e.g., U.S. Pat. Nos. 3,992,518; 5,660,848; and 5,756,115. Additional methods for making modified release formulations are described in, e.g., U.S. Pat. Nos. 5,422,123, 5,601,845, 5,912,013, and 6,194,000, all of which are hereby incorporated by reference.

In some embodiments, the oral dosage form is liquid, semi-liquid, semi-solid, or solid. In some embodiments, the oral dosage form is a gel, pill, tablet, capsule, bead, emulsion, granule, paste, prill, powder, syrup, suspension, slurry, or aerosol.

In some embodiments, the oral dosage form may further comprise an additional agent. In some embodiments, the additional agent is a pharmaceutically acceptable carrier. In some embodiments, the pharmaceutically acceptable carrier is selected from the group consisting of micelles, liposomes, microspheres, nanofibers, and any combination thereof. In some embodiments, the additional agent is a pharmaceutically acceptable excipient. In some embodiments, the pharmaceutically acceptable excipient is selected from the group consisting of a binder, filler, lubricant, dissolution aid, and any combination thereof. In some embodiments, the pharmaceutically acceptable excipient is selected from the group consisting of lactose, microcrystalline cellulose, silicon dioxide, titanium dioxide, stearic acid, starch, sodium starch glycolate, povidone, pregelatinized starch, croscarmellose, ethylcellulose, calcium phosphate, talc, sucrose, calcium stearate, magnesium stearate, hydroxypropyl methylcellulose, shellac, hydrogenated vegetable oil, carnauba wax, beeswax, and any combination thereof.

In some embodiments, the additional agent may be a nutritionally active agent. In some embodiments, the nutritionally active agent is selected from the group consisting of a calcium-containing material, an herbal, a spice, vitamin A, vitamin B, vitamin C, vitamin D, vitamin E, vitamin K, niacin, folic acid, biotin, a mineral, and any combination thereof.

The controlled release dosage form provided by the present invention can adopt a variety of formats. In some embodiments, the controlled release dosage form is administered as oral dosage forms. In some embodiments, the oral dosage form may be a tablet. As used herein the term "tablet" refers generally to tablets, caplets, capsules, including soft gelatin capsules, and lozenges. The average tablet size for round tablets is preferably about 10 mg to 150 mg elemental Mg and for capsule-shaped tablets about 20 mg to 200 mg elemental Mg. The tablet generally may fall into one of three categories: matrix, reservoir and osmotic systems. In some embodiments, the controlled release tablet is based on a reservoir system, wherein the magnesium- and threonate-containing core is encapsulated by a porous membrane coating which, upon hydration, permits magnesium threonate to diffuse through. The effective daily dosage for human use can be about 25 to 1000 mg of magnesium, which corresponds to 303 to 12119 mg of magnesium threonate. The mass range will vary if magnesium and threonate are from compound sources other than magnesium threonate. Because the combined mass of the effective ingredients is generally in gram quantity, an efficient delivery system can provide optimal results.

EXAMPLES

Example 1

Preparation and Dissolution Profiles of Immediate Release Tablets

An example of an immediate release tablet formulation (Formula 1) is shown in Table 2. The Formula 1 tablet was formulated with magnesium L-threonate as magnesium composition, povidone K-90 as binder, microcrystalline cellulose as a glidant, colloidal silicon dioxide as a filler, polyplasdone as a disintegrant, and talc as inert powders.

The release profile of Formula 1 tablets prepared above was examined in a USP type II (paddle) dissolution system at 75 rpm, at a temperature of about 37° C. in 250 mL, in 0.1N HCl (pH 1.1) or acetate buffer (pH 4.5). The amount of released threonic acid over time was measured using high-performance liquid chromatography (HPLC). The amount of released magnesium over time was measured using inductively coupled plasma mass spectroscopy (ICP-MS). The release profiles in pH 1.1 and 4.5 are shown in Table 3 and FIG. 1A.

TABLE 2

| Ingredients | Mg/tablet. | %, wt/wt |
| --- | --- | --- |
| Magnesium L-Threonate | 600.00 | 67.57 |
| Povidone K-90, USP (Plasdone® K-90) | 35.52 | 4.00 |
| Microcrystalline Cellulose, NF (Avicel PH102) | 177.59 | 20.00 |
| Colloidal Silicon Dioxide, NF (CAB - O - SIL® M-5P) | 7.50 | 0.84 |
| Polyplasdone XL10 | 52.39 | 5.90 |
| Talc Powder, USP | 7.50 | 0.84 |
| Magnesium Stearate, NF | 7.50 | 0.84 |
| Total | 888.00 | 100.00 |
| Purified Water, USP* | — | — |

TABLE 3

| | Formula 1 | |
| --- | --- | --- |
| Hour | pH 1.1 % threonate dissolved | pH 4.5 % threonate dissolved |
| 0.5 | 96 | 64 |
| 1 | 101 | 93 |

Example 2

Preparation and Dissolution Profiles of Controlled Release Tablets

An example of a controlled release tablet formulation (Formula 2) is shown in Table 4. The Formula 2 tablet was formulated with magnesium L-threonate as magnesium composition, providone K-90 as binder, microcrystalline cellulose as glidant, colloidal silicon dioxide as filler, carbopol and carboxyl methyl cellulose as swellable materials, Starcap starch, magnesium stearate lubricant, and talc as inert powders.

The release profile of Formula 2 tablets prepared above was examined in a USP type II (paddle) dissolution system at 75 rpm, at a temperature of about 37° C., in 0.1N HCl (pH 1.1), acetate buffer (pH 4.5), or phosphate buffer (pH 6.8). The amount of released threonic acid over time was measured using HPLC. The amount of released magnesium over time was measured using ICP-MS. The release profiles in pH 1.1, 4.5, and 6.8 are shown in Table 5 and FIG. 1B.

TABLE 4

| Ingredients | Mg/tablet. | %, wt/wt |
| --- | --- | --- |
| Magnesium L-Threonate | 600.00 | 67.57 |
| Povidone K-90, USP (Plasdone® K-90) | 53.28 | 6.00 |
| Microcrystalline Cellulose, NF (Avicel PH102) | 102.30 | 11.52 |
| Colloidal Silicon Dioxide, NF (CAB - O - SIL® M-5P) | 7.50 | 0.84 |
| Carbopol 974 P | 31.08 | 3.50 |
| Carboxy methyl cellulose 7 HF, USP | 48.84 | 5.50 |
| Starcap 1500, NF | 30.00 | 3.38 |
| Talc Powder, USP | 7.50 | 0.84 |
| Magnesium Stearate, NF | 7.50 | 0.84 |
| Total | 888.00 | 100.00 |
| Purified Water, USP* | — | — |

TABLE 5

| | Formula 2 | | |
| --- | --- | --- | --- |
| Hour | pH 1.1 % threonate dissolved | pH 4.5 % threonate dissolved | pH 6.8 % threonate dissolved |
| 0 | 0 | 0 | 0 |
| 1 | 30.01 | 30.41 | 36.69 |
| 2 | 42.19 | 47.10 | 56.30 |
| 4 | 67.18 | 84.84 | 89.87 |
| 6 | 74.28 | 102.04 | 101.69 |
| 8 | 78.61 | 106.44 | 98.76 |

Example 3

Dissolution Profiles of Immediate Release and Controlled Release Tablets in Combination A combination of two tablets, one exhibiting an immediate release profile (Formula 1) and one exhibiting a controlled release profile (Formula 2), was immersed in a dissolution medium and the overall dissolution profile was examined in a USP type II (paddle) dissolution system at 75 rpm, at a temperature of about 37° C. The amount of released threonic acid over time was measured using HPLC. The amount of released magnesium over time was measured using ICP-MS. The release profiles in pH 1.1 and 4.5 are shown in Table 6 and FIG. 1C.

TABLE 6

| | Formula 1 + Formula 2 | |
| --- | --- | --- |
| Hour | pH 1.1 % threonate dissolved | pH 4.5 % threonate dissolved |
| 0 | 0 | 0 |
| 1 | 65.5 | 61.7 |
| 2 | 71.5 | 70 |
| 4 | 84.0 | 88.9 |
| 6 | 87.6 | 87.5 |
| 8 | 89.8 | 99.7 |

Example 4

Regulation of Transmitter Release by Calcium and Magnesium

The Probability of transmitter release (Pr) of cultured rat hippocampal neurons was measured by quantification of N-β-Triethylammoniumpropyl)-4-(4-(Dibutylamino) Styryl) Pyridinium Dibromide (FM) dye uptake following a string of 30 single 1 Hertz (Hz) action potentials ($Pr_{1Ap}$). A genetically encoded $Ca^{2+}$ indicator (GCaMP6f) was used. GCaMP6f was fused to a vesicle protein synaptophysin and driven by the CaMKIIα promotor (CaMKIIα-Synaptophysin-GCaMP6f, hereafter SypGCaMP6f for short). GCaMP6f expression may be in the surface of vesicles and thereby may be used to detect the change of local $Ca^{2+}$ concentration of vesicles (Chen et al., 2013). Intracellular calcium concentration was proportional to the intensity of the fluorescent signal after action potential stimulation over the intensity of fluorescent signal without simulation ($\Delta F/F_0$). Intracellular magnesium concentration was quantified by the intensity of MgGreen (MgGrn), a fluorescent dye that was proportional to magnesium concentration (Zhou et al., 2015). The results showed a strong positive correlation between increasing intracellular calcium concentration and the upregulation of Pr, as shown in FIG. 3A, plot 310. Upon an elevation of intracellular magnesium (induced by an increase of extracellular magnesium concentration from 0.8 millimolar (mM) to 1.2 mM for 4 h), the calcium-Pr relationship shifted to the right, as shown in FIG. 3A, plot 320. Not wishing to be bound by theory, this may suggest an inhibitory effect of magnesium on Pr. The results also showed an inverse relationship between intracellular magnesium concentration and Pr when the intracellular calcium concentration was low, as shown in FIG. 3B. was more apparent, as shown in FIG. 3B.

Example 5

Effect of Magnesium Threonate Treatment in Patients with Alzheimer's Disease Fifteen patients with a clinical diagnosis of mild-to-moderate Alzheimer's disease (AD) were treated with magnesium threonate administration for 8 weeks (Wroolie et al., 2017, An 8-week open label trial of magnesium L-threonate (i.e., L-threonic acid magnesium salt) in patients with mild to moderate dementia. Personalized Medicine in Psychiatry 4-6, 7-12). The daily dosage of magnesium L-threonate was 1800 mg as follows: (i) a controlled release oral dosage form of magnesium L-threonate (600 mg) in the morning, and (ii) a combination of the controlled release oral dosage form (600 mg) and an immediate release oral dosage form (600 mg) in the evening. Both the controlled release oral dosage form and the immediate release oral dosage form contained vitamins C and D.

Mini-Mental State Examination

Mini-Mental State Examination (MMSE) scores of the subjects were obtained at baseline (T1), 8 weeks (T2) and 4 months (T3). To obtain the MMSE score, each patient was asked a series of questions designed to test a range of everyday mental skills, including orientation to time, orientation to place, registration, attention and calculation, recall, language, repetition, and complex commands. Results of the study are shown in FIG. 5A. The maximum MMSE score is 30 points. A score of 20 to 24 suggests mild dementia, a score of 13 to 20 suggests moderate dementia, and less than 12 indicates severe dementia. Details on MMSE scoring and evaluation by Folstein et al. (1975) is entirely incorporated by reference herein (Folstein et al., 1975, "Mini-mental state". A practical method for grading the cognitive state of patients for the clinician. Journal of Psychiatric Research 12, 189-198).

Neuropsychiatric Symptoms

The effect of MMSE on neuropsychiatric symptoms was also tested in this study. Specifically, anxiety, depression, and sleep disorder were tested. With magnesium L-threonate treatment, there was a significant reduction in anxiety as determined by Hamilton-Anxiety (HAM–A) questionnaire (−4.22±2.54 SD; p=0.001). Subjects in this trial were recruited based on their cognitive impairment. Anxiety and depression were not inclusion criteria, and although anxiety and depression are common in AD, not all of the subjects had anxiety or depression at baseline. To determine whether magnesium L-threonate treatment reduced depression in those who had depression at baseline, we evaluated baseline Geriatric Depression Scale (GDS) score versus the change in GDS score following treatment. There was a significant negative correlation between baseline GDS score and change of GDS at 2 months (R=−0.695, p=0.006), as shown in FIG. 5B. Those with higher depression at baseline had greater reduction in depression following magnesium L-threonate treatment, indicating that magnesium L-threonate likely affected depression. Similarly, not all subjects had sleep disorder at baseline, but like depression, there was a significant correlation between baseline sleep score and change in sleep score (Pittsburgh Sleep Quality Index; PSQI) following MgT treatment (R=−0.741, p=0.002), as shown in FIG. 5C.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method of administering magnesium threonate to a subject in need of supplementing magnesium, wherein at least a portion of magnesium (Mg) and threonate (T) of said magnesium threonate is present in a salt form of $MgT_2$, the method comprising:
   (a) administering a first oral dosage form comprising magnesium threonate; and (b) administering a combination of (i) said first oral dosage form and (ii) a second oral dosage form comprising magnesium threonate, wherein said first and second oral dosage forms exhibit different in vitro dissolution profiles in a dissolution medium, wherein said first oral dosage form and said combination of said first and second oral dosage forms are administered at two different time points per day, and wherein magnesium threonate is present in an amount between about 200 mg to 2000 mg in each of said first and second oral dosage forms.

2. The method of claim 1, wherein a first in vitro dissolution profile of said first oral dosage form in said dissolution medium is slower than a second in vitro dissolution profile of said second oral dosage form in said dissolution medium.

3. The method of claim 2, wherein:
(a) said first in vitro dissolution profile ranges between (i) about 10% to 35% in about 1 hour, (ii) about 20% to 50% in about 2 hours, (iii) greater than about 80% in about 4 hours, (iv) greater than about 90% in about 6 hours, and (v) greater or equal to about 95% in about 8 hours as measured using a USP type II (paddle) dissolution system at 75 rpm, at a temperature of about 37° C.;
(b) said second in vitro dissolution profile ranges between (i) greater than or equal to about 50% in about 0.5 hour and (ii) greater than or equal to about 80% in about 1 hour as measured using a USP type II (paddle) dissolution system at 75 rpm, at a temperature of about 37° C.; and
(c) said combination of said first and second oral dosage forms exhibits a third in vitro dissolution profile ranging between (i) about 50% to 75% in about 1 hour, (ii) greater than about 60% in about 2 hours, and (iii) greater than about 80% in about 4 hours as measured using a USP type II (paddle) dissolution system at 75 rpm, at a temperature of about 37° C.

4. The method of claim 1, wherein a first in vitro dissolution profile of said first oral dosage form in said dissolution medium is faster than a second in vitro dissolution profile of said second oral dosage form in said dissolution medium.

5. The method of claim 4, wherein:
(a) said first in vitro dissolution profile ranges between (i) greater than or equal to about 50% in about 0.5 hour and (ii) greater than or equal to about 80% in about 1 hour as measured using a USP type II (paddle) dissolution system at 75 rpm, at a temperature of about 37° C.;
(b) said second in vitro dissolution profile ranges between (i) about 10% to 35% in about 1 hour, (ii) about 20% to 50% in about 2 hours, (iii) greater than about 80% in about 4 hours, (iv) greater than about 90% in about 6 hours, and (v) greater or equal to about 95% in about 8 hours as measured using a USP type II (paddle) dissolution system at 75 rpm, at a temperature of about 37° C.; and
(c) said combination of said first and second oral dosage forms exhibits a third in vitro dissolution profile ranging between (i) about 50% to 75% in about 1 hour, (ii) greater than about 60% in about 2 hours, and (iii) greater than about 80% in about 4 hours as measured using a USP type II (paddle) dissolution system at 75 rpm, at a temperature of about 37° C.

6. The method of claim 1, wherein magnesium threonate is present in at least an amount to improve a Mini-Mental State Examination (MMSE) score of said subject.

7. The method of claim 1, wherein said first and second oral dosage forms have substantially the same amount of magnesium threonate.

8. The method of claim 1, wherein each of said first and second oral dosage forms is liquid, semi-liquid, semi-solid, or solid.

9. The method of claim 1, wherein each of said first and second oral dosage forms further comprises an additional agent.

10. The method of claim 9, wherein said additional agent is a pharmaceutically acceptable carrier selected from the group consisting of micelles, liposomes, microspheres, nanofibers, and any combination thereof.

11. The method of claim 9, wherein said additional agent is a pharmaceutically acceptable excipient selected from the group consisting of a binder, filler, lubricant, dissolution aid, and any combination thereof.

12. The method of claim 9, wherein said additional agent is a nutritionally active agent.

13. The method of claim 1, wherein said subject suffers from magnesium deficiency, mild cognitive impairment, short-term memory loss, long-term memory loss, Alzheimer's disease, Parkinson's disease, Huntington's disease, autism, schizophrenia, cognitive decline, depression, dementia, attention deficit hyperactivity disorder (ADHD), amyotrophic lateral sclerosis (ALS), diabetes, cardiovascular disease, hypertension, migraine, glaucoma, mood disorder, stress, anxiety, depression, sleep disorder, metabolic disorder, fatigue, cancer, HIV, hepatitis, spinal cord injury, post-surgery recovery, post-traumatic stress disorder, arthritis, neuropathic pain, inflammation, and/or tremor.

14. A kit for administering magnesium threonate to a subject in need of supplementing magnesium, wherein at least a portion of magnesium (Mg) and threonate (T) of said magnesium threonate is present in a salt form of $MgT_2$, the kit comprising:
(a) two of a first oral dosage form comprising magnesium threonate;
(b) one of a second oral dosage form comprising magnesium threonate; and
(c) a set of instructions for instructing said subject on (i) consuming said first oral dosage form in daytime, and (ii) consuming a combination of said first and second oral dosage forms at once in nighttime,
wherein said first and second oral dosage forms (i) contain magnesium threonate in an amount between about 200 mg to 2000 mg, and (ii) exhibit different in vitro dissolution profiles in a dissolution medium.

15. The kit of claim 14, formulated such that the kit provides an amount of said first and second oral dosage forms to be utilized by said subject for at least one month.

16. The kit of claim 14, wherein a first in vitro dissolution profile of said first oral dosage form in said dissolution medium is slower than a second in vitro dissolution profile of said second oral dosage form in said dissolution medium.

17. The kit of claim 16, wherein:
(a) said first in vitro dissolution profile ranges between (i) about 10 to 35% in about 1 hour, (ii) about 20% to 50% in about 2 hours, (iii) greater than about 80% in about 4 hours, (iv) greater than about 90% in about 6 hours, and (v) greater or equal to about 95% in about 8 hours as measured using a USP type II (paddle) dissolution system at 75 rpm, at a temperature of about 37° C.;
(b) said second in vitro dissolution profile ranges between (i) greater than or equal to about 50% in about 0.5 hour and (ii) greater than or equal to about 80% in about 1 hour as measured using a USP type II (paddle) dissolution system at 75 rpm, at a temperature of about 37° C.; and
(c) said combination of said first and second oral dosage forms exhibits a third in vitro dissolution profile ranging between (i) about 50% to 75% in about 1 hour, (ii) greater than about 60% in about 2 hours, and (iii) greater than about 80% in about 4 hours as measured using a USP type II (paddle) dissolution system at 75 rpm, at a temperature of about 37° C.

18. The kit of claim 14, wherein a first in vitro dissolution profile of said first oral dosage form in said dissolution medium is faster than a second in vitro dissolution profile of said second oral dosage form in said dissolution medium.

19. The kit of claim 14, wherein:
(a) said first in vitro dissolution profile ranges between (i) greater than or equal to about 50% in about 0.5 hour and (ii) greater or equal to about 80% in about 1 hour as measured using a USP type II (paddle) dissolution system at 75 rpm, at a temperature of about 37° C.;
(b) said second in vitro dissolution ranges between (i) about 10% to 35% in about 1 hour, (ii) about 20% to 50% in about 2 hours, (iii) greater than about 80% in about 4 hours, (iv) greater than about 90% in about 6 hours, and (v) greater or equal to about 95% in about 8 hours as measured using a USP type II (paddle) dissolution system at 75 rpm, at a temperature of about 37° C.; and
(c) said combination of said first and second oral dosage forms exhibits a third in vitro dissolution profile ranging between (i) about 50% to 75% in about 1 hour, (ii) greater than about 60% in about 2 hours, and (iii) greater than about 80% in about 4 hours as measured using a USP type II (paddle) dissolution system at 75 rpm, at a temperature of about 37° C.

* * * * *